(12) United States Patent
Wustman

(10) Patent No.: US 9,119,845 B2
(45) Date of Patent: *Sep. 1, 2015

(54) METHOD FOR THE TREATMENT OF NEUROLOGICAL DISORDERS BY ENHANCING THE ACTIVITY OF BETA-GLUCOCEREBROSIDASE

(75) Inventor: Brandon Alan Wustman, San Diego, CA (US)

(73) Assignee: Amicus Therapeautics, Inc., Cranbury, NJ (US)

( * ) Notice: Subject to any disclaimer, the term of this patent is extended or adjusted under 35 U.S.C. 154(b) by 1333 days.

This patent is subject to a terminal disclaimer.

(21) Appl. No.: 12/941,468

(22) Filed: Nov. 8, 2010

(65) Prior Publication Data

US 2011/0052613 A1    Mar. 3, 2011

Related U.S. Application Data

(63) Continuation of application No. 11/768,043, filed on Jun. 25, 2007, now Pat. No. 7,829,579.

(60) Provisional application No. 60/815,952, filed on Jun. 23, 2006.

(51) Int. Cl.
| | | |
|---|---|---|
| A61K 31/445 | (2006.01) | |
| A61K 31/713 | (2006.01) | |
| A61K 31/437 | (2006.01) | |
| A61K 31/45  | (2006.01) | |
| A61K 31/194 | (2006.01) | |

(52) U.S. Cl.
CPC ............. *A61K 31/445* (2013.01); *A61K 31/194* (2013.01); *A61K 31/437* (2013.01); *A61K 31/45* (2013.01); *A61K 31/713* (2013.01); *A61K 2300/00* (2013.01)

(58) Field of Classification Search
CPC .......................... A61K 31/445; A61K 31/713
See application file for complete search history.

(56) References Cited

U.S. PATENT DOCUMENTS

| 6,583,158 B1 | 6/2003 | Fan et al. |
| 6,916,829 B2 | 7/2005 | Fan et al. |
| 2002/0035072 A1 | 3/2002 | Fan et al. |
| 2003/0119874 A1 | 6/2003 | Fan et al. |
| 2007/0281975 A1 | 12/2007 | Mugrage et al. |

FOREIGN PATENT DOCUMENTS

| GB | 2 354 946 A | 4/2001 |
| WO | 2004 069190 A | 8/2004 |
| WO | 2005046611 A2 | 5/2005 |
| WO | 2006 133446 A | 12/2006 |
| WO | 2008 144773 A | 11/2008 |

OTHER PUBLICATIONS

Ichikawa et al. J. Am. Chem. Soc., 1998, vol. 120, pp. 3007-3018.*
Selkoe, D.J., Nature Cell Biology, Nov. 2004, vol. 6, No. 11, pp. 1054-1061.
Webster's Ninth New Collegiate Dictionary, 2002, Definition of Prevention, p. 1.
Schlossmacher et al., New England Journal of Medicine, Feb. 2005, vol. 352, Issue 7, pp. 729-731.
Agid et al., Movement Disorders, 1999, vol. 14, No. 6, pp. 911-913.
Aharon-Peretz et al., "Mutations in the Glucocerebrosidase Gene and Parkinson's Disease in Ashkenazi Jews", The New England Journal of Medicine, 351:1972-1977 (2004).
Butters et al., "Therapeutic Applications of Imino Sugars in Lysosomal Storage Disorders," Current Topics in Medicinal Chemistry, 3:561-74 (2003).
Clark et al., "Pilot Association Study of the β-Glucocerebrosidase N370S Allele and Parkinson's Disease in Subjects of Jewish Ethnicity," Movement Disorders, 20(1):100-103 (2005).
Farrer et al., "Glucosidase-beta variations and Lewy body disorders," Parkinsonism and Related Disorders, 15 (6):414-416 (2009); Epub (Oct. 1, 2008).
Goker-Alpan et al., "Parkinsonism among Gaucher disease carriers," J. Med Genet, 41:937-940 (2004).
Hruska et al., Gaucher Disease and the Synucleinopathies, J. of Biomed and Biotech, 2006:1-6 (2006).
Lwin et al., "Glucocerebrosidase mutations in subjects with parkinsonism," Molecular Genetics and Metabolism 81:70-73 (2004).
Office Action dated May 15, 2008 for U.S. Appl. No. 11/449,528.
Office Action dated Nov. 10, 2008 for U.S. Appl. No. 11/449,528.
Office Action dated Mar. 25, 2009 for U.S. Appl. No. 11/449,528.
Office Action-Advisory Action dated May 19, 2009 for U.S. Appl. No. 11/449,528.
Office Action dated Aug. 6, 2009 for U.S. Appl. No. 11/449,528.
Office Action—Interview Summary dated Oct. 21, 2009 for U.S. Appl. No. 11/449,528.
Office Action-Final dated Mar. 24, 2010 for U.S. Appl. No. 11/449,528.
Ruvinov et al., "Monovalent Cations Partially Repair a Conformational Defect in a Mutant Tryptophan Synthase α2β2 Complex (β-E109A)*," The Journal of Biological Chemistry 270(29):17333-17338 (1995).

(Continued)

*Primary Examiner* — Samira Jean-Louis
(74) *Attorney, Agent, or Firm* — Servilla Whitney LLC

(57) ABSTRACT

Provided is a method of increasing the stability of wild-type β-glucocerebrosidase. Also provided are methods of treating and/or preventing an individual having a neurological disease in which increased expression or activity of β-glucocerebrosidase in the central nervous system would be beneficial. This method includes administering an effective amount of a pharmacologic chaperone for β-glucocerebrosidase, with the proviso that the individual does not have a mutation in the gene encoding β-glucocerebrosidase. Further provided are β-glucocerebrosidase inhibitors which have been identified as specific pharmacologic chaperones and which have been shown to increase activity of β-glucocerebrosidase in vivo in the central nervous system.

17 Claims, 6 Drawing Sheets

(56) References Cited

OTHER PUBLICATIONS

Sidransky, E., "Gaucher disease: complexity in a "simple" disorder," Molecular Genetics and Metabolism 83:6-15 (2004).

Sidransky, E., "Gaucher disease and parkinsonism," Molecular Genetics and Metabolism 854:302-304 (2005).

Sawkar et al., "Chemical chaperones increase the cellular activity of N370S β-glucosidase: A therapeutic strategy for Gaucher disease," Proceedings of the National Academy of Sciences of USA, National Academy of Science, Washington, DC, US, vol. 99, No. 24, Nov. 26, 2002, pp. 15428-15433.

Tayebi et al., "Gaucher Disease with Parkinsonism Manifestations: Does Glucocerebrosidase Deficiency Contribute to Vulnerability to Parkinsonism?" Mol. Genet. Metab. 79(2):104-9 (2003).

The Michael J. Fox Foundation for Parkinson's Research, Letter to Brandon Wustman, PhD and Sean Clark, PhD, Dec. 8, 2006.

The Michael J. Fox Foundation for Parkinson's Research, "Principal Investigator on Application: Brandon Wustman," Target Validation 2006 RFA.

LJ Ozelius et al., "LRRK2 G2019S as a Cause of Parkinson's Disease in Ashkenazi Jews," New England Journal of Medicine, 354(4):424-425 (2006).

Wong et al., "Neuropathology Provides Clues to the Pathophysiology of Gaucher Disease," Molecular Genetics and Metabolism 82:192-207 (2004).

Emyr Lloyd-Evans et al., "Glucosylceramide and glucosylsphingosine modulate calcium mobilization from brain microsomes via different mechanisms," The Journal of Biological Chemistry, vol. 278, No. 26, pp. 23594-23599, 2003.

Bernard Brugg et al., "Ceramide induces apoptosis in cultured mesencephalic neurons," Journal of Neurochemistry, vol. 66, pp. 733-739, 1996.

Eduard Orvisky et al., "Glucosylsphingosine accumulation in tissues from patients with Gaucher disease: correlation with phenotype and genotype", Molecular Genetics and Metabolism, vol. 76, issue 4, pp. 262-270, 2002.

Eduard Korkotian et al., "Elevation of intracellular glucosylceramide levels results in an increase in endoplasmic reticulum density and in functional calcium stores in cultured neurons", The Journal of Biological Chemistry, vol. 274, No. 31, pp. 21673-21678, (1999).

Michael J. Eblan et al., "Glucocerebrosidase mutations are not found in association with LRRK2 G2019S in subjects with parkinsonism", Neuroscience Letters, Elsevier, 404(1-2):163-165, 2006.

Doug A. Brooks, "Getting into the fold", Nature Chemical Biology, 3(2):84-85, 2007.

\* cited by examiner

1. Units in nmole 4MU/mg protein per hour
2. Values reported with standard error

A.

B.

C.

METHOD FOR THE TREATMENT OF NEUROLOGICAL DISORDERS BY ENHANCING THE ACTIVITY OF BETA-GLUCOCEREBROSIDASE

CROSS-REFERENCE TO RELATED APPLICATIONS

This application is a continuation application of Ser. No. 11/768,043, filed Jun. 25, 2007 which claims priority from U.S. Provisional Patent Application Ser. No. 60/815,952, filed Jun. 23, 2006, the disclosure of which is incorporated herein by reference in its entirety.

FIELD OF THE INVENTION

The invention relates to methods of increasing the activity of the lysosomal enzyme β-glucocerebrosidase for the treatment of α-synucleinopathies such as Parkinson's disease, and for the treatment of Niemann-Pick Disease type C. The invention provides specific pharmacological chaperones for β-glucocerebrosidase, which increase cytosolic trafficking, and enzymatic activity of β-glucocerebrosidase, presumably by stabilizing the enzyme.

BACKGROUND OF THE INVENTION

Protein Aggregation in Neurodegenerative Diseases

In neurons, the proteasomal and lysosomal systems work in concert to maintain protein homeostasis by degrading damaged, misfolded or excess proteins. Many neurodegenerative diseases associated with pathologic aggregation of proteins or lipids show impaired proteasomal and lysosomal function, including Alzheimer's disease, Parkinson's disease, Huntington's disease, amyotrophic lateral sclerosis (ALS), Gaucher disease, Tay Sachs, Farber, Niemann-Pick Types A, B & C, $G_{M1}$ Gangliosidosis, $G_{M2}$ Gangliosidosis, and MPS-I. Protein aggregation in neurons is particularly dire since neurons are unable to regenerate following neurodegeneration or apoptosis that arises from neuronal stress or other causes associated with the aggregation.

Protein Aggregation and Lysosomes.

The lysosomal system is critical in preventing the accumulation of protein aggregates that are difficult for the proteasomes to degrade. The importance of lysosomes in degrading protein aggregates is supported by the numerous reports of lysosomal proteins and autophagic markers co-localizing in the same structure with protein aggregates found in human brains (Bjørkøy et al., *J Cell Biol.* 2005; 171(4):603-14; Tribl et al., *Mol Cell Proteomics,* 2005; 4(7): 945-57; Wong et al., *Mol Genet Metab,* 2004. 82(3):192-207; Zhou, *J Biol Chem.* 2004. 279(37): 39155-64). In particular, neutralization of the acidic compartments (lysosomes) leads to the accumulation of α-synuclein (α-syn) aggregates and exacerbates α-syn toxicity in postmitotic neuronal cells (Lee, *J Neurosci,* 2004; 24(8): 1888-96). Pathologic α-syn aggregation is associated with Parkinson's disease and other α-synucleinopathies. Lastly, lysosome dysfunction has been reported for transgenic mouse models that accumulate α-syn (Meredith et al., *Brain Res,* 2002; 956(1):156-65; Rockenstein et al., *J Neurosci Res,* 2005; 80(2): 247-59).

Protein Aggregation and Proteasomes.

The proteasome is integral in degrading cytosolic proteins. Proteasomal-mediated degradation begins with the modification of substrates by polyubiquitin chains, which targets proteolysis by the 26S proteasome, a multicatalytic protease complex. Studies have revealed that ubiquitin is a component of many of the filamentous inclusion bodies characteristic of neurodegenerative diseases, suggesting activation of a common neuronal response in this type of disease process (Lowe et al., *Neuropathol Appl Neurobiol.* 1990; 16: 281-91). Genetic studies, including identification of mutations in genes associated with familial Parkinson's (SNCA), and the presence of proteinaceous cytoplasmic inclusions in spared dopaminergic nigral neurons in sporadic cases of Parkinson's, have suggested an important role for ubiquitin-proteasome system and aberrant protein degradation in this disease (Betarbet et al., *Exp Neural.* 2005; 191 Suppl 1:S17-27).

Since it is well-established that accumulation or aggregation of numerous misfolded proteins and lipids in a cell, including neurons, leads to endoplasmic reticulum and cell stress, increased amounts of polyubiquitin, a cell "stress" protein, suggests that the proteasomal system is overactivated. However, an alternate theory for disruptions in neuronal homeostasis in CNS aggregation diseases is due to suppression of the ubiquitin/proteasome pathway (Rocca et al., *Molecular Biology of the Cell.* 2001; 12: 1293-1301). Both in vivo and in vitro studies have linked α-syn aggregation and oxidative stress, both hallmarks of Parkinson's disease, to a compromised ubiquitin-proteasome system and Parkinson's disease pathogenesis. (Lev et al., *Neurosci Lett.* 2006; 399(1-2):27-32). Specifically, exposure to reactive oxygen species (ROS) combined with proteasomal inhibition increased α-syn aggregate formation over proteasomal inhibition alone. Moreover, structural and functional defects in 26/20S proteasomes, with accumulation and aggregation of potentially cytotoxic abnormal proteins, have been identified in the substantia nigra pars compacta of patients with sporadic Parkinson's disease (McKnaught et al., *Ann Neurol.* 2003; 53 Suppl 3:S73-84). In addition, mutations in SNCA that cause the protein to misfold and resist proteasomal degradation are highly associated with familial Parkinson's disease. It also was shown that aggregated α-syn inhibits proteasomal function by interacting with S6', a subunit of the proteasome (Snyder et al., *J Mol Neurosci.* 2004; 24(3):425-42). Lastly, proteasomal function is decreased in brains of subjects with Parkinson's disease as well as in brains from individuals and animals lacking parkin, which is an E3 ubiquitin ligase, and is an integral part of the ubiquitin proteasomal system.

Thus, a defect in protein handling by the proteasome appears to be a common factor in sporadic and the various familial forms of Parkinson's disease. This same conclusion was drawn from experiments in which combinations of a proteasome inhibitor with agents that induce protein misfolding were added to a culture of dopaminergic neurons (Mytilineou et al., *J Neural Transm.* 2004; 111(10-11):1237-51). Preferential loss of dopamine neurons and cell death was markedly increased when the two were combined.

Even low levels of proteasome inhibition can lead to down regulation of the ubiquitin proteasome system and activation of the lysosomal system or autophagic response (Ding et al., *J Neurochem,* 2003; 86(2):489-97; Iwata et al., *Proc Natl Acad Sci USA,* 2005; 102(37):13135-40; Butler et al., *Rejuvenation Res.* 2005; 8(4):227-37). It has been proposed that an imbalance between endogenous ER chaperones and damaged/denatured/misfolded proteins, leading to accumulation of the latter, can result in senescence, inhibition of the proteasome (leading to apoptosis), or necrosis, depending on the severity of the imbalance (Soti et al., *Aging Cell.* 2003; 2: 39-45). This hypothesis is referred to as the "toxic protein accumulation hypothesis."

Lipid Defects and Neurodegenerative Diseases

It is well known that lipid accumulation is associated with neurodegeneration, as is evident from lysosomal storage disorders such as Gaucher, Tay Sachs, Farber, Niemann-Pick Types A, B and C, $G_{M1}$ Gangliosidosis, and MPS-I diseases. However, other lipid accumulation in neurological diseases in which there are no deficiencies in the lysosomal hydrolases also has been observed. As one example, pathological accumulations of lactosylceramide, GlcCer, $G_{M2}$-ganglioside, and asialo-$G_{M2}$ are found in Niemann-Pick Type C disease, which is a lysosomal cholesterol storage disease that is not associated with deficient acid sphingomyelinase due to missense mutations in the gene encoding the enzyme (Vanier et al., *Brain Pathology.* 1998; 8: 163-74). This accumulation may be caused by other mechanisms, such as defective lipid trafficking. A healthy endosomal trafficking system is critical to neuronal function (Buckley et al., *J Physiol,* 2000; 525(Pt 1):11-9). Disruption of glycosphingolipid metabolism, including GlcCer, impairs cellular trafficking and causes cholesterol sequestration and accumulation (Pagano et al., *Traffic,* 2000; 1(11): 807-15; Sillence et al., *J Lipid Res,* 2002; 43(11):1837-1845; Helms et al., *Traffic,* 2004; 5(4):247-54). Accumulated glycolipids form "lipid rafts" that can sequester proteins important in maintaining normal trafficking in the endosomal system (Pagano, supra). Moreover, the defective trafficking of lipids observed in fibroblasts from Niemann-Pick Type C cells can be reversed by treatment with a potent inhibitor of glycosphingolipid biosynthesis (Lachmann et al., *Neurobiol Dis,* 2004; 16(3):654-8), further underscoring the involvement of GlcCer and other lipids in the pathology of this disease.

Further, association with lipid rafts is required for normal localization of α-syn to its native cellular location, the synapses (Fortin et al., *J Neurosci,* 2004; 24(30):6715-23). Mutations associated with the pathology of Parkinson's disease disrupt this association. Thus changes in lipid raft composition that also disrupt this association could contribute to Parkinson's disease by impairing normal localization and distribution of α-syn as well.

Glycosphingolipids Help to Seed Protein Aggregation

Alpha-synuclein has a high affinity for gangliosides, and wild-type α-syn forms SDS stable complexes with gangliosides that have GlcCer at their core (Zimran et al., *N Engl J Med,* 2005; 352(7):728-31). Soluble forms of both α-syn and β-amyloid protein bind strongly to $G_{M1}$, potentially seeding aggregation (Yanagisawa et al., *Neurobiol Aging,* 1998; 19(1 Suppl):S65-7; Yanagisawa et al., *Nat Med,* 1995; 1(10):1062-6; Lee et al., *J Biol Chem,* 2002; 277(1): 671-8; Hayashi et al., *J Neurosci.* 2004; May 19; 24(20):4894-902). Recently, cell based experiments have demonstrated mutations of the lysosomal enzyme β-glucocerebrosidase (GCase) may increase the risk for developing Parkinsons's disease (Aharon-Peretz, et al., *N Engl J Med,* 2004; 351(19):1972-7; Goker-Alpan et al., *J Med Genet,* 2004; 41(12):937-40; Clark et al., *Mov Disord,* 2005; 20(1):100-3; Eblan et al., *Mov Disord,* 2005; 31:31). While carriers of mutant alleles do not appear to accumulate significant levels of glucosylceramide (histologically), subtle changes in glycosphingolipid metabolism could increase the risk for Parkinson's disease in these individuals by, e.g., disrupting autophagic responses to normal aggregates, or inhibiting the proteasomes. In addition, patients with type 1 Gaucher disease (due to GCase deficiencies) and parkinsonism/dementia exhibited α-syn positive inclusions in hippocampal CA2-4 neurons; one patient had brainstem-type and cortical-type Lewy bodies, and one had marked neuronal loss of substantia nigra neurons (Wong et al., *Mol. Genet. Metabol.* 2004; 38: 192-207).

Similarly, in vitro, large unilamellar vesicles of brain lipids readily associated with soluble N-terminal huntingtin exon 1 fragments, the pathologic protein which accumulates in Huntington's disease, and stimulated fibrillogenesis of mutant huntingtin aggregates (Suopanki et al., *J Neurochem.* 2006; 96(3):870-84). Lastly, in a mouse model for Sandhoff disease ($G_{M2}$ Gangliosidosis), α-syn and β-synuclein accumulate in neurons in addition to $G_{M2}$ gangliosides (Suzuki et al., *Neuroreport.,* 2003; 14(4):551-4). Thus, manipulating ganglioside metabolism could affect the propensity for proteins to form aggregates.

The foregoing suggests that lipid interactions in vivo could influence misfolding of proteins and may play a significant role in neurodegenerative disease pathogenesis.

Lipid and/or Protein Accumulation and Inflammation

Inflammation has been increasingly recognized to play an important role in the pathogenesis of Parkinson's disease. Inflammatory and immune, or even autoimmune, stigmata, have been described in post-mortem brains of Parkinson's disease patients. Alpha-syn aggregates could activate microglial cells, resulting in chronic inflammation leading to neurodegeneration (Wersinger et al., *Curr Med Chem.* 2006; 13(5):591-602).

Pharmacological Chaperones Derived from Specific Enzyme Inhibitors Rescue Mutant Enzymes and Enhance Wild-Type Enzymes It has previously been shown that the binding of small molecule inhibitors of enzymes associated with LSDs can increase the stability of both mutant enzymes and the corresponding wild-type enzymes (see U.S. Pat. Nos. 6,274,597; 6,583,158; 6,589,964; 6,599,919; 6,916,829, and 7,141,582 all incorporated herein by reference). In particular, it was discovered that administration of small molecule derivatives of glucose and galactose, which are specific, selective competitive inhibitors for several target lysosomal enzymes, effectively increased the stability of the enzymes in cells in vitro and, thus, increased the amount of the enzyme in the lysosome as determined by measuring enzyme activity. Thus, by increasing the amount of enzyme in the lysosome, hydrolysis of the enzyme substrates is expected to increase. The original theory behind this strategy was as follows: since the mutant enzyme protein is unstable in the ER (Ishii et al., *Biochem. Biophys. Res. Comm.* 1996; 220: 812-815), the enzyme protein is retarded in the normal transport pathway (ER→Golgi apparatus→endosomes→lysosome) and prematurely degraded. Therefore, a compound which binds to and increases the stability of a mutant enzyme, may serve as a "chaperone" for the enzyme and increase the amount that can exit the ER and move to the lysosomes. In addition, because the folding and trafficking of some wild-type proteins is incomplete, with up to 70% of some wild-type proteins being degraded in some instances prior to reaching their final cellular location, the chaperones can be used to stabilize wild-type enzymes and increase the amount of enzyme which can exit the ER and be trafficked to the native cellular locations.

Since some enzyme inhibitors are known to bind specifically to the catalytic center of the enzyme (the "active site"), resulting in stabilization of enzyme conformation in vitro, these inhibitors were proposed, somewhat paradoxically, to be effective chaperones that could help restore exit from the ER, trafficking to the lysosomes, and hydrolytic activity. These specific pharmacological chaperones were designated "active site-specific chaperones (ASSCs)" or "specific pharmacological chaperones" since they bound in the active site of the enzyme in a specific fashion and do not have a general affect on all proteins.

A method for treating Parkinson's disease in individuals having mutations in lysosomal GCase, and hence, a reduction in GCase activity, is described in co-pending U.S. application Ser. No. 11/449,528 filed on Jun. 8, 2006. Although the rescue of mutant lysosomal enzymes can reverse the pathology of certain diseases, there remains a need to reduce the pathology of diseases that do not involve particular lysosomal enzyme mutations, but for which an increase in lysosomal enzymes would be beneficial.

SUMMARY OF THE INVENTION

The present invention provides a method for the treatment or prevention of a neurological disorder in an individual, wherein the neurological disorder is associated with protein and lipid aggregation within the cells of the central nervous system, by administering an effective amount of a specific pharmacological chaperone for GCase, but wherein the neurological disorder is not associated with a mutant GCase.

In one embodiment, the present invention provides a method for enhancing intracellular folding and processing, and hence, activity of wild type GCase by exposing the neurons to an effective amount of a specific pharmacological chaperone for GCase.

In on aspect of this embodiment, the neurological disorder to be treated is an α-synucleinopathy.

In specific embodiments, the α-synucleinopathy is Parkinson's disease, Lewy Body Disease, Multiple System Atrophy, Hallervorden-Spatz disease, or Frontotemporal Dementia.

In another aspect of this embodiment, the neurological disorder to be treated is Parkinson's disease.

In another aspect of this embodiment, the neurological disorder to be treated is Niemann-Pick Type C disease (NPCD).

In one embodiment of the invention, the pharmacological chaperone is a reversible inhibitor of GCase.

In a specific embodiment of this aspect of the invention, the pharmacological chaperone is an isofagomine compound, such as isofagomine or C-nonyl-isofagomine, C-benzyl isofagomine, or N-alkyl derivatives of isofagomine as provided herein. In another specific embodiment, the pharmacological chaperone is a glucoimidazole compound such as glucoimidazole, (5R,6R,7S,8S)-5-hydroxymethyl-2-octyl-5,6,7,8-tetrahydroimidazo[1,2-a]pyridine-6,7,8-triol or (5R,6R,7S,8S)-5-Hydroxymethyl-2-(3,3-dimethylbutyl)-5,6,7,8-tetrahydroimidazo[1,2-a]pyridine-6,7,8-triol.

In a further embodiment, the increase in GCase enzymatic activity is at least, but not limited to, 1.2, 1.5, 2, 3, or 5 fold over basal levels.

In an alternative embodiment in which the neurodegenerative disorder is Niemann-Pick Type C disease, the second therapeutic agent is selected from the group consisting of allopreganolone, a statin, a fenofibrate, niacin; ezetimibe, a binding resin, a specific pharmacological chaperone for β-hexosaminidase A or acid β-galactosidase, 2-N-acetylamino-isofagomine, 1,2-dideoxy-2-acetamido-nojirimycin, nagstatin, 4-epi-isofagomine, and 1-deoxygalactonojirimycin.

The present invention also provides a method of treating or preventing a neurodegenerative disorder in an individual having or at risk of developing a neurodegenerative disorder, where the individual does not have a mutation in the gene encoding GCase, by administering to the individual a pharmacological chaperone that binds to GCase.

The invention also provides a method for combination therapy with the GCase chaperone and other therapeutic agents for treatment of the neurological disorder. In addition, the invention provides compositions of matter comprising an admixture of a GCase pharmacological chaperone and another therapeutic agent. In an embodiment in which the neurological disorder is Parkinsons's Disease, parkinsonism, or Lewy Body Dementia, the second therapeutic agent is selected from the group consisting of levodopa, an anticholinergic, a Catechol-O-methyl transferase (COMT) inhibitor, a dopamine receptor agonist, a monoamine oxidase inhibitor (MAOI), a peripheral decarboxylase inhibitor, and an anti-inflammatory.

BRIEF DESCRIPTION OF THE DRAWINGS

The patent or application file contains at least one drawing executed in color. Copies of the patent or patent application publication with color drawing(s) will be provided by the Office upon request and payment of the necessary fee.

FIG. 1 shows GCase enhancement in spleen, lung, brain and liver of normal C57BL6 mice treated with 200 mg/kg/day of isofagomine tartrate (IFG; AT2101) for 4 weeks.

FIG. 2 shows changes in GCase activity following administration of isofagomine tartrate to healthy volunteers.

FIG. 3A-C. FIG. 3A shows results from a vehicle treated control; FIGS. 3B and 3C show results from mice treated with 2 mg/kg daily for 3 months.

FIG. 4A-C. FIG. 4A shows results from a vehicle treated control; FIGS. 4B and 4C show results from mice treated with 2 mg/kg daily for 3 months.

FIG. 5A-D.

FIG. 6A-B.

DETAILED DESCRIPTION

The present invention relates to the discovery that a specific pharmacological chaperone can increase the activity of wild-type GCase to a sufficient level to inhibit, even to the point of prevention, pathology associated with the build up of aggregated proteins and substrate lipids. This in turn, can be used to treat neurological risk factors, conditions, or disorders associated with the aggregation of those substrate proteins and lipids within the cells of the central nervous system.

Specifically, the present invention provides a method of administering one or more pharmacological chaperones for GCase to an individual diagnosed, at risk, or suspected to have a neurological disorder that could be benefited by increased activity of GCase. Suitable pharmacological chaperones include any compound(s) which, following administration to an individual, will specifically bind to GCase, increase the stability and trafficking of GCase, and thereby increase GCase activity in the lysosome, provided that the neurological disease or disorder is not associated with a mutation in the gene encoding GCase. Enhancing enzymatic function in the cells of the central nervous system, presumably as a result of a more stable intracellular form of GCase, increases metabolism of GCase-associated peptides and GCase lipid substrates within the cells, which is useful in the treatment of neurological disorders such as Parkinson's disease and Niemann-Pick Type C disease, neither of which are associated with deficient GCase activity.

Figure 2:
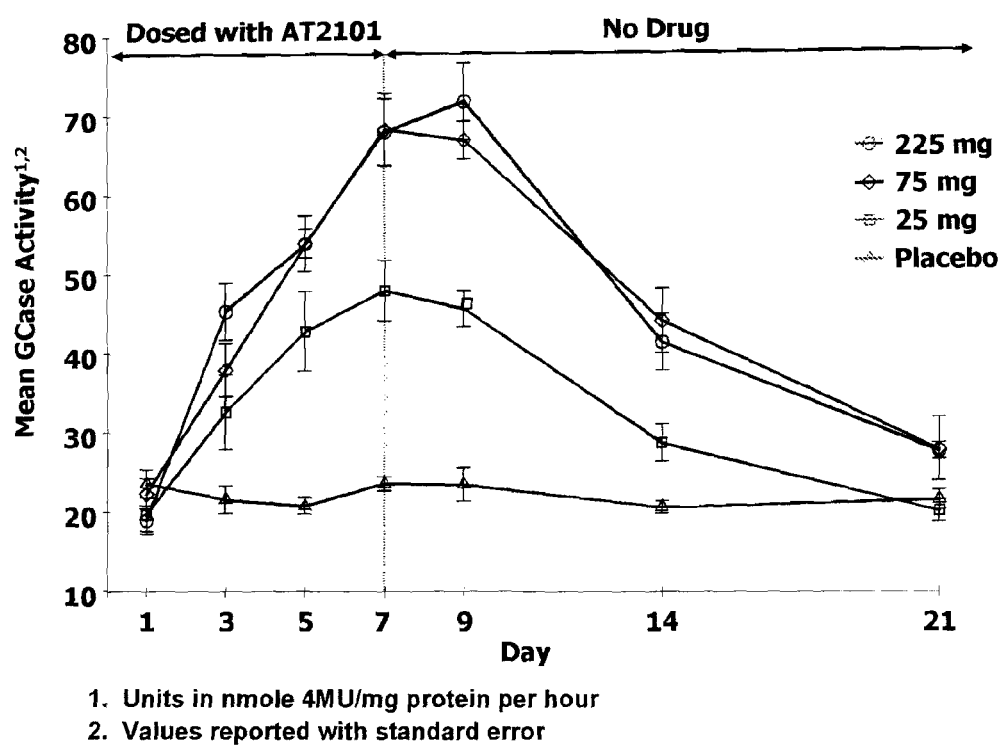
FIG. 2.

The invention is based, in part, on the discovery of a pharmacological chaperone's ability to promote significantly increased wild-type protein activity in humans. This phenomenon is highly specific to the protein specifically bound by the particular pharmacological chaperone, in contrast to methods that operate generally on expression of all proteins. The experimental results that underlie the present invention include the observations that pharmacological chaperones can increase endogenous wild-type protein activity by at least about 20-25%, in some cases by at least about 50%, and in specific embodiments by at least about 90%, and even 100%. This level of increase in vivo was not observed with cells in tissue culture, and comes as a surprise, given the expectation that normal physiological processes would buffer the effects of pharmacological chaperones in vivo. There was no basis to expect that a pharmacological chaperone could increase the level of activity of a wild type protein in vivo in a human by at least 20-25%, and particularly, by at least about 50%. As exemplified infra, administration of isofagomine to healthy subjects resulted in a dose-dependent increase in GCase activity (FIG. 2). At some concentrations, which were readily tested using routine dose-response testing, the level of increase in enzyme activity increased by at least 50% to up to 100%.

The present invention came about from the known link between lysosomal enzyme insufficiency and neurological disease states (e.g., Types 2 and 3 Gaucher disease), and the fact that protein and/or lipid aggregation and neuronal death/degeneration is observed in many non-LSD neurodegenerative disorders, such as described earlier in the Background section. Thus, the present invention unexpectedly exploits the ability to increase the activity of non-deficient lysosomal enzymes to increase clearance of protein aggregates, particularly aggregates in which proteins (or fragments thereof including monomers) are associated with lipid substrates of the lysosomal enzyme, such as, for example, SCNA with GlcCer. Reducing the lipid substrate to which the pathologic protein associates will likely reduce aggregation of the pathologic protein, thereby ameliorating neurological symptoms and/or preventing neuronal death or neurodegeneration. Alternatively, the enhancement of GCase activity may reduce the concentration of a lipid that in turn provides a cellular environment better able to control the degradation of aggregation-prone proteins.

The invention also unexpectedly exploits the ability to increase the activity of non-deficient lysosomal enzymes to alter the lipid profile in neurons in which there is accumulation of GlcCer, glucosylsphingosine (GlcSph; or other lipids whose levels change in response to GCase activity due to abnormal lipid metabolism) by a mechanism other than reduced GCase activity, or due to abnormalities in intracellular lipid trafficking.

The use of specific pharmacological chaperones according to the present invention has potential advantages over other methods of supplementing GCase, such as by administration of recombinant enzyme (ERT) or using substrate reduction therapy (SRT) with, e.g., Zavesca®, since the former must be administered directly into the brain via a catheter, and the latter inhibits synthesis of numerous glycolipids, and not just those that may be beneficial to decrease for one particular neurological disorder. Zavesca® has severe side effects and it use is limited to patients who cannot tolerate ERT. Therefore, these treatments are less effective than a treatment than can enhance hydrolase activity ubiquitiously of the enzyme of choice.

DEFINITIONS

Biological and Clinical

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use the invention.

The terms "neurological disorder," or "neurodegenerative disorder" refer to any central nervous system (CNS) or peripheral nervous system (PNS) disease that is associated with neuronal or glial cell defects including, but not limited to, neuronal loss, neuronal degeneration, neuronal demyelination, gliosis (including macro- and micro-gliosis), or neuronal or extraneuronal accumulation of aberrant proteins or toxins (e.g., β-amyloid, or α-synuclein). The neurological disorder can be chronic or acute. Exemplary neurological disorders include but are not limited to Gaucher disease, Parkinson's disease, Alzheimer's disease, amyotrophic lateral sclerosis (ALS), multiple sclerosis (MS), Huntington's disease, Fredrich's ataxia, Mild Cognitive Impairment, Cerebral Amyloid Angiopathy, Parkinsonism Disease, Lewy Body Disease, Frontotemporal Dementia (FTD) Multiple System Atrophy (MSA), Progressive Supranuclear Palsy, and movement disorders (including ataxia, cerebral palsy, choreoathetosis, dystonia, Tourette's syndrome, kernicterus) and tremor disorders, and leukodystrophies (including adrenoleukodystrophy, metachromatic leukodystrophy, Canavan disease, Alexander disease, Pelizaeus-Merzbacher disease), neuronal ceroid lipofucsinoses, ataxia telangectasia and Rett Syndrome.

In particular, the term "α-synucleinopathy" refers to diseases associated with aberrant accumulation of α-syn, including but not limited to parkinsonism, Parkinson's disease, Lewy Body Disease, Multiple System Atrophy, Hallervorden-Spatz disease, and Frontotemporal Dementia.

A "neurological disorder associated with mutations in a lysosomal enzyme" refers to any neurological disorder in which mutations in one or more lysosomal gene or genes are also present when assessed in individuals having the neurological disorder, compared with individuals not having the neurological disorder. In one, non-limiting example, the neurological disorder associated with Gba mutations is a lysosomal storage disease, such as Gaucher disease, or a neurodegenerative disease associated with a heterozygous Gba mutation, such as a subset of patients with Parkinson's disease. One aspect of the present invention is that it relates to treatment of a neurological disorder that does not involve a mutation in Gba.

The term "increase in lysosomal activity" refers to increasing the amount of a lysosomal enzyme polypeptide that adopts a functional conformation in the ER in a cell contacted with a pharmacological chaperone specific for a lysosomal enzyme, relative to lysosomal enzyme expression in a cell (preferably of the same cell-type) not contacted with the pharmacological chaperone specific for the lysosomal enzyme, therefore, increasing the rate of lipid and/or protein metabolism mediated by the lysosome in a cell, relative to the rate prior to administration of the pharmacological chaperone(s). While an increase in activity of a single lysosomal enzyme in the lysosome will result in an increase in lysosomal activity, the invention advantageously provides for increase activity of a number of lysosomal enzymes, resulting in broad lipid and/or protein metabolism.

The aforementioned term also means increasing the efficiency of transport of a wild-type lysosomal enzyme polypeptide from the ER to the lysosome in a cell contacted with a pharmacological chaperone specific for the lysosomal enzyme, relative to the efficiency of transport of endogenous wild-type lysosomal enzyme polypeptide in a cell (preferably of the same cell-type) not contacted with the pharmacological chaperone specific for the lysosomal enzyme.

The terms "lysosomal enzyme" or "lysosome enzyme" refer to any enzyme that functions in the lysosome. Lysosomal enzymes include, but are not limited to α-galactosidase A; β-glucosidase; α-glucosidase; β-hexosaminidase A; β-hexosaminidase B; α-L-iduronidase; β-galactosidase; β-glucuronidase; α-glucuronidase; α-fucosidase; sulfatases; acid ceramidases; NPC1; acid sphingomyelinase; prosaposin (saposins A,B,C,D); cathepsins (A, D, H, S, Z); H(+)-ATPases; sialidase; β-galactocerebrosidase; arylsulfatase; iduronate-2-sulfatase; heparan N-sulfatase; α-N-acetylglucosaminidase; α-glucosaminide N-acetyltransferase; N-acetylglucosamine-6-sulfate sulfatase; N-acetylgalactosamine-6-sulfate sulfatase; arylsulfatase B; acid α-mannosidase; acid β-mannosidase; acid α-L-fucosidase; α-N-acetyl-neuraminidase; β-N-acetylglucosaminidase; and α-N-acetylgalactosaminidase.

The terms or "wild-type lysosomal enzyme" refer to the normal endogenous lysosomal polypeptides, and the nucleotide sequences encoding the lysosomal enzyme polypeptides, and any other nucleotide sequence that encodes a lysosomal enzyme polypeptide (having the same functional properties and binding affinities as the aforementioned polypeptide), such as allelic variants in normal individuals, that have the ability to achieve a functional conformation in the ER, achieve lysosomal localization, and exhibit wild-type activity (i.e., decrease lysosomal enzyme substrate concentrations). A wild-type lysosomal enzyme is not a mutant or mutated protein or enzyme. However, the invention does not exclude the possibility that there may be more than one wild-type allele for a lysosomal enzyme. This term thus includes polymorphisms that have no detrimental effect on function or activity of the lysosomal enzyme.

Certain tests may evaluate attributes of a protein that may or may not correspond to its actual in vivo function, but nevertheless are surrogates of protein functionality, and wild-type behavior in such tests is an acceptable consequence of the protein rescue or enhancement techniques of the invention. One such activity in accordance with the invention is appropriate transport of a wild type lysosomal enzyme from the endoplasmic reticulum to the lysosome, its native location.

As used herein the terms "mutated protein" or "mutated enzyme" refer to proteins or enzymes translated from genes containing genetic mutations that result in protein sequences altered from the wild type sequence which have an effect on protein function or activity. In a specific embodiment, such mutations result in the inability of the protein to achieve a stable conformation under the conditions normally present in the ER. The failure to achieve this conformation results in these proteins being degraded, or aggregated, rather than being transported through their normal pathway in the protein transport system to their proper location within the cell. Mutations other than conformational mutations also can result in decreased enzymatic activity or a more rapid turnover.

As used herein, the terms "pharmacological chaperone" or sometimes "specific pharmacological chaperone" ("SPC") refer to a molecule, such as a small molecule, protein, peptide, nucleic acid, or carbohydrate, that specifically binds to a protein and has one or more of the following effects: (i) enhancing the formation of a stable molecular conformation of the protein; (ii) inducing trafficking of the protein from the ER to another cellular location, preferably a native cellular location, i.e., preventing ER-associated degradation of the protein; (iii) preventing aggregation of misfolded proteins; and/or (iv) restoring or enhancing at least partial wild-type function and/or activity to the protein. A compound that specifically binds to, e.g. a lysosomal enzyme, means that it binds to and exerts a chaperone effect on the lysosomal enzyme and not a generic group of related or unrelated proteins. Thus a pharmacological chaperone for a lysosomal enzyme is a molecule that binds preferentially to that lysosomal enzyme, resulting in proper folding, trafficking, non-aggregation, and activity of that lysosomal enzyme. As used herein, this term does not refer to endogenous chaperones, such as BiP, or to non-specific agents which have demonstrated chaperone activity against various proteins, such as DMSO or deuterated water.

In one, non-limiting embodiment, the pharmacological chaperone may be an inhibitor, or structurally similar analog thereof, of GCase. The pharmacological chaperone may be selected from the list including, but not limited to, isofagomine; C-nonyl-isofagomine; C-benzyl-isofagomine; N-butyl-isofagomine; N-(3-cyclohexylpropyl)-isofagomine; N-(3-phenylpropyl)-isofagomine; N-((2Z,6Z)-3,7,11-trimethyldodeca-2,6,10-trienyl)-isofagomine; N-dodecyl-isofagomine (N-dodecyl-IFG); 2-N-acetamido-isofagomine; 2-hydroxy-isofagomine; 2-N-acetylamino-isofagomine; and analogs and derivatives thereof.

A "competitive inhibitor" of an enzyme can refer to a compound that structurally resembles the chemical structure and molecular geometry of the enzyme substrate to bind the enzyme in approximately the same location as the substrate. Thus, the inhibitor competes for the same active site as the substrate molecule, thus increasing the Km. Competitive inhibition is usually reversible if sufficient substrate molecules are available to displace the inhibitor, i.e., competitive inhibitors can bind reversibly. Therefore, the amount of enzyme inhibition depends upon the inhibitor concentration, substrate concentration, and the relative affinities of the inhibitor and substrate for the active site.

Non-classical competitive inhibition occurs when the inhibitor binds to a site that is remote to the active site, creating a conformational change in the enzyme such that the substrate can no longer bind to it. In non-classical competitive inhibition, the binding of substrate at the active site prevents the binding of inhibitor at a separate site and vice versa. This includes allosteric inhibition.

A "non-competitive inhibitor" refers to a compound that forms strong bonds with an enzyme and may not be displaced by the addition of excess substrate, i.e., non-competitive inhibitors may be irreversible. A noncompetitive inhibitor may be bonded at, near, or remote from the active site of an enzyme or protein, and in connection with enzymes, has no effect on the Km but decreases the Vmax.

Uncompetitive inhibition refers to a situation in which inhibitor binds only to the ES complex. The enzyme becomes inactive when inhibitor binds. This differs from non-classical competitive inhibitors which can bind to the enzyme in the absence of substrate.

The term "Vmax" refers to the maximum initial velocity of an enzyme-catalyzed reaction, i.e., at saturating substrate levels.

The term "Km" is the substrate concentration required to achieve ½ Vmax.

An enzyme "enhancer" is a compound that binds to a lysosomal enzyme and increases the enzymatic reaction rate.

The term "stabilize a lysosomal enzyme" refers to the ability of a pharmacological chaperone to induce or stabilize a conformation of a wild-type or functionally identical lysosomal enzyme protein. The term "functionally identical" means that while there may be minor variations in the conformation (almost all proteins exhibit some conformational flexibility in their physiological state), conformational flexibility does not result in (1) protein aggregation, (2) elimination through the endoplasmic reticulum-associated degradation pathway, (3) impairment of protein function, e.g., degrading damaged, misfolded or excess proteins, and/or (4) improper transport within the cell, e.g., localization to a lysosome within the cytosol, to a greater or lesser degree than that of the wild-type protein. Stabilization can be determined by any one of (i) increased enzyme half-life in the cell; (ii) increased levels of the enzyme in the lysosome; or (ii) increased hydrolytic activity as measured in cellular lysates using an artificial substrate.

As used herein, the term "efficiency of transport" refers to the ability of a mutant protein to be transported out of the endoplasmic reticulum to its native location within the cell, cell membrane, or into the extracellular environment. The native location for a lysosomal enzyme is the lysosome.

As used herein, the terms "patient" or "patient population" refer to individual(s) diagnosed as having a neurological disorder or at risk of developing a neurological disorder. Diagnosing neurological disorders includes identification of symptoms of decreased neurological function. Symptoms include, but are not limited to, tremor, trembling in hands, arms, legs, jaw, and face; rigidity, or stiffness of the limbs and trunk; bradykinesia, or slowness of movement; postural instability, or impaired balance and coordination; amnesia; aphasia; apraxia; agnosia; personality changes; depression; hallucinations; and delusions. Methods of diagnosing neurological disorders are known to those skilled in the art. In one embodiment, the neurological disorder may be sporadic, with no association with a mutant genotype. In another embodiment, the neurological disorder may be due to an increased aggregation of lysosome enzyme substrates, or other proteins or fragments thereof, within the cells of the CNS or PNS in patients who are not deficient in lysosomal hydrolases, i.e., do not have a mutation in a gene encoding a lysosomal hydrolase which results in reduced enzyme activity. Although these patients may have a mutation in a non-lysosomal enzyme, e.g., α-syn, which promotes aggregation. In another, non-limiting embodiment, the neurological disorder may have a genetic basis that is not addressed by any one, or combination, of chaperones used. For example, a patient may have a genotype consisting of a homozygous null mutation for a lysosomal enzyme in which no functional protein is produced. In this case, increasing the activity of other, non-mutated lysosomal enzymes according to the method of the present invention may compensate for the deficient lysosomal enzyme.

A "responder" is an individual diagnosed with a neurological disorder associated with a protein and lipid aggregates in cells of the central nervous system, and treated according to the presently claimed method who exhibits an improvement in, amelioration, or prevention of, one or more clinical symptoms, or improvement or reversal of one or more surrogate clinical markers. In a specific embodiment, changes in the levels of α-synuclein in plasma, including increases and decreases compared to normal controls, is a surrogate marker for a positive response to pharmacological chaperone therapy for GCase.

The terms "therapeutically effective dose" and "effective amount" refer to the amount of the specific pharmacological chaperone that is sufficient to result in a therapeutic response. A therapeutic response may be any response that a practitioner (e.g., a clinician) will recognize as an effective response to the therapy, including the foregoing symptoms and surrogate clinical markers. Thus, a therapeutic response will generally be an amelioration of one or more symptoms of a disease or disorder, such as those described above.

The phrase "pharmaceutically acceptable" refers to molecular entities and compositions that are physiologically tolerable and do not typically produce untoward reactions when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition.

The terms "about" and "approximately" generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

Chemical

The term "alkyl" refers to a straight or branched $C_1$-$C_{20}$ hydrocarbon group consisting solely of carbon and hydrogen atoms, containing no unsaturation, and which is attached to the rest of the molecule by a single bond, e.g., methyl, ethyl, n-propyl, 1-methylethyl (isopropyl), n-butyl, n-pentyl, 1,1-dimethylethyl (t-butyl). The alkyls used herein are preferably $C_1$-$C_8$ alkyls.

The term "alkenyl" refers to a $C_2$-$C_{20}$ aliphatic hydrocarbon group containing at least one carbon-carbon double bond and which may be a straight or branched chain, e.g., ethenyl, 1-propenyl, 2-propenyl(allyl), iso-propenyl, 2-methyl-1-propenyl, 1-butenyl, 2-butenyl.

The term "alkynyl" refers to monovalent, unbranched or branched hydrocarbon chain having one or more triple bonds therein. The triple bond of an alkynyl group can be unconjugated or conjugated to another unsaturated group. Suitable alkynyl groups include, but are not limited to, $(C_2-C_8)$alkynyl groups, such as ethynyl, propynyl, butynyl, pentynyl, hexynyl, methylpropynyl, 4-methyl-1-butynyl,4-propyl-2-pentynyl-, and 4-butyl-2-hexynyl. An alkynyl group can be unsubstituted or substituted with one or two suitable substituents.

The term "cycloalkyl" denotes an unsaturated, non-aromatic mono- or multicyclic hydrocarbon ring system such as cyclopropyl, cyclobutyl, cyclopentyl, cyclohexyl. Examples of multicyclic cycloalkyl groups include perhydronapththyl, adamantyl and norbornyl groups bridged cyclic group or sprirobicyclic groups, e.g., spiro (4,4) non-2-yl.

The term "cycloalkylalkyl" refers to a cycloalkyl as defined above directly attached to an alkyl group as defined above, that results in the creation of a stable structure such as cyclopropylmethyl, cyclobutylethyl, cyclopentylethyl.

The term "alkyl ether" refers to an alkyl group or cycloalkyl group as defined above having at least one oxygen incorporated into the alkyl chain, e.g., methyl ethyl ether, diethyl ether, tetrahydrofuran.

The term "alkyl amine" refers to an alkyl group or a cycloalkyl group as defined above having at least one nitrogen atom, e.g., n-butyl amine and tetrahydrooxazine.

The term "aryl" refers to aromatic radicals having in the range of about 6 to about 14 carbon atoms such as phenyl, naphthyl, tetrahydronapthyl, indanyl, biphenyl.

The term "arylalkyl" refers to an aryl group as defined above directly bonded to an alkyl group as defined above, e.g., —$CH_2C_6H_5$, and —$C_2H_4C_6H_5$.

The term "heterocyclic" refers to a stable 3- to 15-membered ring radical which consists of carbon atoms and from one to five heteroatoms selected from the group consisting of nitrogen, phosphorus, oxygen and sulfur. For purposes of this invention, the heterocyclic ring radical may be a monocyclic, bicyclic or tricyclic ring system, which may include fused, bridged or Spiro ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heteroaromatic or heteroaryl aromatic). Examples of such heterocyclic ring radicals include, but are not limited to, azetidinyl, acridinyl, benzodioxolyl, benzodioxanyl, benzofurnyl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, quinoxalinyl, quinolinyl, isoquinolinyl, tetrazoyl, imidazolyl, tetrahydroisouinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxasolidinyl, triazolyl, indanyl, isoxazolyl, isoxasolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, furyl, tetrahydrofurtyl, tetrahydropyranyl, thienyl, benzothienyl, thiamorpholinyl, thiamorpholinyl sulfoxide thiamorpholinyl sulfone, dioxaphospholanyl, oxadiazolyl, chromanyl, isochromanyl.

The heterocyclic ring radical may be attached to the main structure at any heteroatom or carbon atom that results in the creation of a stable structure.

The term "heteroaryl" refers to a heterocyclic ring wherein the ring is aromatic.

The term "heteroarylalkyl" refers to heteroaryl ring radical as defined above directly bonded to alkyl group. The heteroarylalkyl radical may be attached to the main structure at any carbon atom from alkyl group that results in the creation of a stable structure.

The term "heterocyclyl" refers to a heterocylic ring radical as defined above. The heterocyclyl ring radical may be attached to the main structure at any heteroatom or carbon atom that results in the creation of a stable structure.

The term "heterocyclylalkyl" refers to a heterocylic ring radical as defined above directly bonded to alkyl group. The heterocyclylalkyl radical may be attached to the main structure at carbon atom in the alkyl group that results in the creation of a stable structure.

The substituents in the "substituted alkyl", "substituted alkenyl," "substituted alkynyl," "substituted cycloalkyl," "substituted cycloalkalkyl," "substituted cyclocalkenyl," "substituted arylalkyl," "substituted aryl," "substituted heterocyclic ring," "substituted heteroaryl ring," "substituted heteroarylalkyl," or substituted heterocyclylalkyl ring," may be the same or different with one or more selected from the groups hydrogen, hydroxy, halogen, carboxyl, cyano, amino, nitro, oxo (=O), thio (=S), or optionally substituted groups selected from alkyl, alkoxy, alkenyl, alkynyl, aryl, arylalkyl, cycloalkyl, aryl, heteroaryl, heteroarylalkyl, heterocyclic ring, —$COOR^x$, —$C(O)R^x$, —$C(S)R^x$, —$C(O)NR^xR^y$, —$C(O)ONR^xR^y$, —$NR^xCONR^yR^z$, —$N(R^x)SOR^y$, —$N(R^x)SO_2R^y$, —(=N—N($R^x)R^y$), —$NR^xC(O)OR^y$, —$NR^xR^y$, —$NR^xC(O)R^y$—, —$NR^xC(S)R^y$ —$NR^xC(S)NR^yR^z$, —$SONR^xR^y$—, —$SO_2NR^xR^y$—, —$OR^x$, —$OR^xC(O)NR^yR^z$, —$OR^xC(O)OR^y$—, —$OC(O)R^x$, —$OC(O)NR^xR^y$, —$R^xNR^yR^z$, —$R^xR^yR^z$, —$R^xNR^yC(O)R^z$, —$R^xOR^y$, —$R^xC(O)OR^y$, —$R^xC(O)NR^yR^z$, —$R^xC(O)R^x$, —$R^xOC(O)R^y$, —$SR^x$, —$SOR^x$, —$SO_2R^x$, —$ONO_2$, wherein $R^x$, $R^y$ and $R^z$ in each of the above groups can be hydrogen atom, substituted or unsubstituted alkyl, haloalkyl, substituted or unsubstituted arylalkyl, substituted or unsubstituted aryl, substituted or unsubstituted cycloalkyl, substituted or unsubstituted cycloalkalkyl substituted or unsubstituted heterocyclic ring, substituted or unsubstituted heterocyclylalkyl, substituted or unsubstituted heteroaryl or substituted or unsubstituted heteroarylalkyl.

The term "halogen" refers to radicals of fluorine, chlorine, bromine and iodine.

The term "a short flexible linker" refers to linkers with linear length of about 6 Å to about 12 Å, preferably about 9 Å. A short flexible linker comprises molecules bonded to each other, for example, but not limited to, carbon bound to carbon and carbon bound to a heteroatom such as nitrogen, oxygen, or sulfur, wherein the molecules bonded together can rotate around the axis of the bond. In a particular embodiment, the flexible linker can adopt different conformations and orientations that can alter the distance between molecular domains connected by the short flexible linker.

Chaperone Therapy for Neurodegenerative Disorders

In one series of embodiments, small molecule pharmacological chaperones increase the stability of a non-mutant GCase in the ER, increase trafficking to the lysosome, and increase the enzyme's half-life by stabilizing the protein in the lysosome. This strategy may result in an increase in enzymatic activity or enzyme function in the lysosome, and hence, increased lysosomal activity. Lipid metabolism, such as GlcCer metabolism can thus be modulated by increasing GCase activity, leading to a reduced level of GlcCer in the cell when compared to a cell not contacted with the chaperone. As discussed above, this strategy is expected decrease the amount of α-syn, and/or will ameliorate pathological accumulation of GlcCer or any disruptive lipid imbalance involving GlcCer in cells, particularly neurons.

Chaperones for GCase.

There are numerous compounds that can be used, alone or in combination, as pharmacological chaperones to increase lysosomal activity by increasing the activity of GCase. As discussed above, competitive inhibitors for GCase previously have been shown to increase GCase activity. Accordingly, it is anticipated that these and other inhibitors of GCase may be useful for decreasing the amount of α-syn, possibly by increasing GCase activity in the lysosome, although other mechanisms are possible.

Isofagomine (IFG; (3R,4R,5R)-5-(hydroxymethyl)-3,4-piperidinediol) refers to a compound having the following structure:

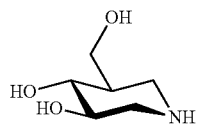

Isofagomine tartrate has recently been described in commonly-owned U.S. patent application Ser. No. 11/752,658, filed on May 23, 2007, and has been assigned CAS number 919364-56-0. Isofagomine also may be prepared in the form of other acid addition salts made with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrate, phosphate, borates, citrates, benzoates, ascorbates, salicylates and the like). Such salts can be formed as known to those skilled in the art.

N-alkyl derivatives of isofagomine are also contemplated for use in the present invention. Such compounds are described in U.S. Pat. No. 6,046,214 to Kristiansen et al., and U.S. Pat. No. 5,844,102 to Sierks et al. In an additional embodiment, the isofagomine derivative has the following Formula I:

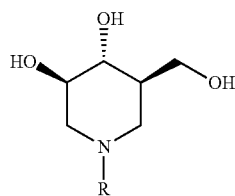

wherein:

R is $C_{1-7}$haloalkyl, $C_{1-10}$alkyl, $C_{3-7}$alkenylalkyl, $C_{2-7}$alkoxyalkyl, $C_{1-7}$carbamoylalkyl or X—Ar$^1$;

X is —(CH)$_n$— or $C_2$-$C_3$ alkenylene;

n is an integer from 0-3;

Ar$^1$ is

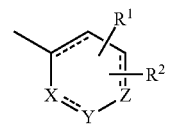

wherein $R_1$ and $R_2$ are independently selected from hydrogen, halo, $C_{1-3}$alkyl, $C_{1-3}$alkoxy, amino, nitro, heteroaryl, aryl, or cyano; X and Z are independently C, N, O, or S when Y is C, N, O, or S; or X and Z are independently C, N—R$^3$, O or S when Y is a single bond connecting X and Z wherein R$^3$ is $C_{1-3}$alkyl or hydrogen, or pharmaceutically acceptable salts thereof.

In yet a further embodiment, the isofagomine derivative has the following Formula Ia:

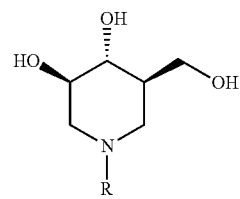

wherein:

R is $C_{1-10}$alkyl, $C_{3-7}$alkenylalkyl, $C_{2-7}$alkoxyalkyl, or X—Ar;

X is —(CH)$_n$— or $C_2$-$C_3$ alkenylene;

n is an integer from 0-3;

Ar is

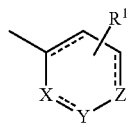

wherein X and Z is C, N, O, or S; Y is C, N, O, S or a single bond connecting X and Z; $R_1$ is a hydrogen, halo, $C_{1-3}$alkyl, $C_{1-3}$alkoxy, amino, nitro, aryl, or cyano, or pharmaceutically acceptable salts thereof.

Specific N-alkyl derivatives include N-dodecyl isofagomine and those provided in Table 1 below:

TABLE 1

| Compound | R |
|---|---|
| 1 | (structure) |
| 2 | (structure) |

TABLE 1-continued
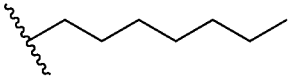 [SMILES: *CCCCCCC]
| Compound | R |
|---|---|
| 3 | 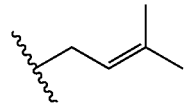 [SMILES: *CC=C(C)C] |
| 4 | 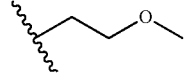 [SMILES: *CCOC] |
| 5 | 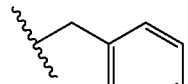 |
| 6 | 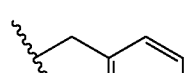 |
| 7 | 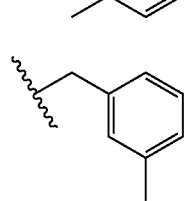 |
| 8 | 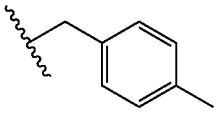 [SMILES: *Cc1ccc(C)cc1] |
| 9 | 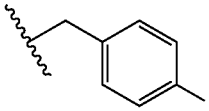 |
| 10 | 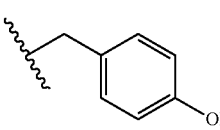 |
| 11 | 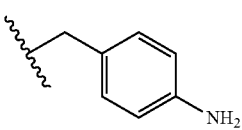 [SMILES: *Cc1ccc(N)cc1] |
| 12 | 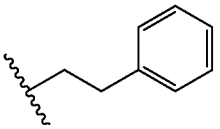 [SMILES: *CCc1ccccc1] |
TABLE 1-continued
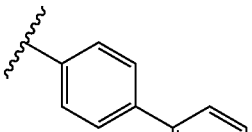
| Compound | R |
|---|---|
| 13 | 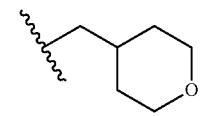 |
| 14 | 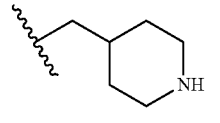 [SMILES: *CC1CCNCC1] |
| 15 | 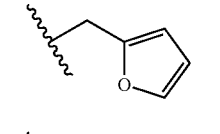 |
| 16 | 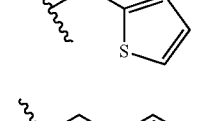 |
| 17 | 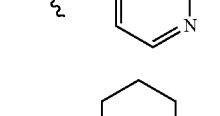 |
| 18 |  |
| 19 | 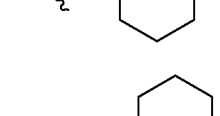 |
| 20 | 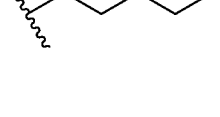 |
| 21 |  |
| 22 | |

TABLE 1-continued

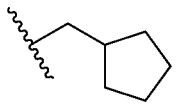 [SMILES: *CC1CCCC1]

| Compound | R |
|---|---|
| 23 | 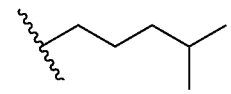 [SMILES: *CCCC(C)C] |
| 24 | (isohexyl group) |
| 25 | 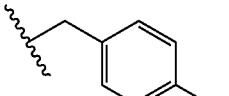 |

The compounds are named as follows: (3R,4R,5R)-5-(hydroxymethyl)-1-propylpiperidine-3,4-diol (1); (3R,4R,5R)-5-(hydroxymethyl)-1-pentylpiperidine-3,4-diol (2); (3R,4R,5R)-1-heptyl-5-(hydroxymethyl)piperidine-3,4-diol (3); (3R,4R,5R)-5-(hydroxymethyl)-1-(3-methylbut-2-enyl)piperidine-3,4-diol (4); (3R,4R,5R)-5-(hydroxymethyl)-1-(2-methoxyethyl)piperidine-3,4-diol (5); (3R,4R,5R)-1-benzyl-5-(hydroxymethyl)piperidine-3,4-diol (6); (3R,4R,5R)-5-(hydroxymethyl)-1-(2-methylbenzyl)piperidine-3,4-diol (7); (3R,4R,5R)-5-(hydroxymethyl)-1-(3-methylbenzyl)piperidine-3,4-diol (8); (3R,4R,5R)-5-(hydroxymethyl)-1-(4-methylbenzyl)piperidine-3,4-diol (9); (3R,4R,5R)-1-(4-fluorobenzyl)-5-(hydroxymethyl)piperidine-3,4-diol (10); (3R,4R,5R)-5-(hydroxymethyl)-1-(4-methoxybenzyl) piperidine-3,4-diol (11); (3R,4R,5R)-1-(4-aminobenzyl)-5-(hydroxymethyl)piperidine-3,4-diol (12); (3R,4R,5R)-5-(hydroxymethyl)-1-(2-phenylethyl)piperidine-3,4-diol (13); (3R,4R,5R)-1-(biphenyl-4-ylmethyl)-5-(hydroxymethyl)piperidine-3,4-diol (14); (3R,4R,5R)-5-(hydroxymethyl)-1-((tetrahydro-2H-pyran-4-yl)methyl)piperidine-3,4-diol (15); (3R,4R,5R)-5-(hydroxymethyl)-1-(piperidin-4-ylmethyl)piperidine-3,4-diol (16); (3R,4R,5R)-1-(furan-2-ylmethyl)-5-(hydroxymethyl)piperidine-3,4-diol (17); (3R,4R,5R)-5-(hydroxymethyl)-1-(thiophen-2-ylmethyl)piperidine-3,4-diol (18); (3R,4R,5R)-5-(hydroxymethyl)-1-(pyridin-4-ylmethyl)piperidine-3,4-diol (19); (3R,4R,5R)-1-cyclohexyl-5-(hydroxymethyl)piperidine-3,4-diol (20); (3R,4R,5R)-1-(cyclohexylmethyl)-5-(hydroxymethyl)piperidine-3,4-diol (21); (3R,4R,5R)-1-(2-cyclohexylethyl)-5-(hydroxymethyl)piperidine-3,4-diol (22); (3R,4R,5R)-1-(cyclopentylmethyl)-5-(hydroxymethyl)piperidine-3,4-diol (23); (3R,4R,5R)-5-(hydroxymethyl)-1-(4-methylpentyl)piperidine-3,4-diol (24); and (3R,4R,5R)-5-(hydroxymethyl)-1-(4-nitrobenzyl)piperidine-3,4-diol (25).

Additional inhibition data for these compounds towards GCase, and or some cellular enhancement data for GCase, are provided in Table 2 below:

TABLE 2

| Compound | IC$_{50}$ (μM) (n = 3) | Ki (μM) (n = 3) | EC$_{50}$ (μM) (n = 3) |
|---|---|---|---|
| 1 | 35.81 ± 6.69 | 14.84 ± 2.77 | 65.9 ± 15.6 |
| 2 | 979.9 ± 137 | 406.06 ± 56.34 | 266.1 ± 47.7 |
| 3 | 41.70 ± 3.05 | 17.28 ± 1.26 | 9.99 ± 2.56 |
| 4 | 4.00 ± .035 | 1.66 ± .015 | 63.0 ± 14.1 |
| 5 | 5.99 ± 0.11 | 2.48 ± 0.05 | 60.7 ± 0.11 |
| 6 | 200.27 ± 61.78 | 82.99 ± 25.6 | 115.3 ± 18.5 |
| 7 | 69.47 ± 8.18 | 28.79 ± 3.39 | 46.4 ± 8.7 |
| 8 | 12.7 ± 2.14 | 5.26 ± 0.89 | 11.6 ± 2.4 |
| 9 | 129.63 ± 14.71 | 53.72 ± 6.10 | 144.8 ± 2.9 |
| 10 | 269.80 ± 39.21 | 111.8 ± 16.25 | 70.6 ± 2.1 |
| 11 | nd | nd | nd |
| 12 | 9.36 ± 1.16 | 3.88 ± 0.48 | 7.7 ± 1.5 |
| 13 | 7.5 ± 0.82 | 3.11 ± 0.34 | 2.2 ± 0.1 |
| 14 | nd | nd | nd |
| 15 | 49.22 ± 5.5 | 20.39 ± 2.28 | 68.3 ± 5.7 |
| 16 | 1.07 ± 0.02 | 0.44 ± 0.01 | 6.9 ± 1.5 |
| 17 | 280.07 ± 62.55 | 116.39 ± 25.92 | 65.6 ± 15.7 |
| 18 | 27.55 ± 0.49 | 11.42 ± 0.2 | 139.0 ± 27.8 |
| 19 | 19.35 ± 1.24 | 8.02 ± 0.51 | 35.0 ± 3.6 |
| 20 | nd | nd | nd |
| 21 | nd | nd | nd |
| 22 | nd | nd | nd |
| 23 | 15.63 ± 2.2 | 6.48 ± .091 | 18.8 ± 2.8 |
| 24 | 2.13 ± 0.17 | 0.88 ± 0.07 | 30.5 ± 4.8 |
| 25 | 44.96 ± 3.99 | 18.63 ± 1.65 | 16.4 ± 2.2 | nd = not done

Methods of synthesizing isofagomine and some derivatives are well known in the and are described in the following: Jespersen et al., *Angew. Chem., Int. ed. Engl.* 1994; 33: 1778-9; Dong et al., *Biochem.* 1996; 35:2788; Lundgren et al., *Diabetes.* 1996; 45:S2 521; Schuster et al., *Bioorg Med Chem Lett.* 1999; 9(4):615-8; Andersch et al., *Chem. Eur. J* 2001; 7: 3744-3747; Jakobsen et al., *Bioorg Med Chem.* 2001; 9: 733-44; 36:435; Pandy et al., *Synthesis.* 2001: 1263-1267; Zhou et al., *Org Lett.* 2001; 3(2):201-3; Best et al., *Can. J. Chem./Rev. Can. Chim.* 2002; 80(8): 857-865; Huizhen et al., *J. Carbohydr Chem.* 2004; 23: 223-238; Mehta et al., *Tetrahedron Letters* 2005; 41(30):5747-5751; Ouchi et al., *J Org Chem.* 2005; 70(13):5207-14; and most recently, Meloncelli et al., *Australian Journal of Chemistry.* 2006; 59(11) 827-833. Synthesis of the L stereoisomer is described in Panfil et al., *J. Carbohydr Chem.* 2006; 25: 673-84.

Specifically, the N-alkyl isofagomine derivatives described above can be made by routes known in the art to alkylate secondary amines, such as by either displacement of a mesylate (from the corresponding commercially available alcohols) or by reductive amination. A brief description of these methods is provided below.

General Method for Alkylation

After 1 equivalent of the alcohol and 1.5 equivalent of triethylamine are dissolved in CH2Cl2, methanesulfonyl chloride (1.2 equivalent) is added dropwise to the reaction mixture at 0° C. The reaction mixture is stirred at RT for 2 hours, and then poured into water and extracted with CH2Cl2. The solvent is removed to give the crude product which was used directly for next step.

3 equivalent of the crude product from the previous step and 1 equivalent of 5-(hydroxymethyl)piperidine-3,4-diol and K2CO3 (5 equivalents) are suspended in DMF, and the mixture is stirred and heated at 70° C. for 3 days. The reaction mixture is filtered and the solvent is removed to give a crude product. The crude product and silica gel are suspended in MeOH.HCl solution, and stirred at RT for 30 mins. The solvent is removed to give a solid, which is packed to the top of silica gel column. The final compound is eluted by Ethyl Acetate/MeOH/aq ammonia (9/1/0.2).

General Method for Reductive Amination 3 equivalent of aldehyde or ketone and 1 equivalent of 5-(hydroxymethyl)piperidine-3,4-diol are suspended in methanol, then Na(CN)BH3 (6 eq) is added. The reaction mixture is stirred at RT for 3 days. The reaction mixture is filtered and the solvent was removed to give a crude product. The crude product and silica gel is suspended in MeOH.HCl solution, and stirred at RT for 30 mins. The solvent is removed to give a solid, which is packed to the top of silica gel column. The final compound was eluted by Ethyl Acetate/MeOH/aq ammonia (9/1/0.2).

General Method for Nitro Reduction 5-(Hydroxymethyl)-1-(4-nitrobenzyl)piperidine-3,4-diol and Zinc (10 eq) are stirred in MeOH.HCl solution at RT for one hour. The solvent is removed to give a crude product, which is purified by silica gel column.

Since these compounds specifically bind to and enhance GCase, they also can be used for the treatment of Gaucher disease and other neurological disorders associated with mutations in GCase.

Other chaperones for GCase include glucoimidazole, polyhydroxylcycloalkylamines and derivatives, and hydroxyl piperidine derivatives, which are described in pending U.S. published applications 2005/0130972 and 2005/0137223, and corresponding PCT publications WO 2005/046611 and WO 2005/046612, all filed on Nov. 12, 2004 and incorporated herein by reference. Glucoimidazole and derivatives are represented by the following Formula II:

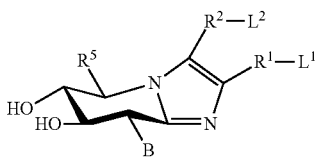

wherein B is selected from the group consisting of hydrogen, hydroxy, acetamino, and halogen;

$R^1$ and $R^2$ optionally present are short, flexible linkers linear length of about 6 Å to about 12 Å, preferably about 9 Å. $R^1$ and $R^2$ can also be independently selected from the group consisting of $C_2$-$C_6$ substituted or unsubstituted alkyl optionally interrupted by one or more moieties chosen from the group consisting of NH, NHCOO, NHCONH, NHCSO, NHCSNH, CONH, NHCO, $NR^3$, O, S, $S(O)_m$ and —$S(O)_m NR^3$; $C_2$-$C_6$ substituted or unsubstituted alkenyl optionally interrupted by one or more moieties chosen from the group consisting of NH, NHCOO, NHCONH, NHCSO, NHCSNH, CONH, NHCO, $NR^3$, O, S, $S(O)_m$ and —$S(O)_m NR^3$; $C_2$-$C_6$ substituted or unsubstituted alkynyl optionally interrupted by one or more moieties chosen from the group consisting of NH, NHCOO, NHCONH, NHCSO, NHCSNH, CONH, NHCO, $NR^3$, O, S, $S(O)_m$ and —$S(O)_m NR^3$, wherein m is 1 or 2, and $R^3$ is independently selected from each occurrence from the groups consisting of hydrogen substituted or unsubstituted alkyl, substituted or unsubstituted alkenyl; substituted or unsubstituted cycloalkyl, substituted or unsubstituted cycloalkenyl; substituted or unsubstituted aryl; substituted or unsubstituted arylalkyl; substituted or unsubstituted heteroaryl; substituted or unsubstituted heterocyclic; substituted or unsubstituted heterocyclalkyl; substituted or unsubstituted heteroarylalkyl.

In addition, $R^1$-$L^1$ and/or $R^2$-$L^2$ can be hydrogen.

$R^5$ represents a hydrogen, hydroxy, or hydroxylmethyl;

$L^1$ and $L^2$ are lipophilic groups selected from the group consisting of $C_3$-$C_{12}$ substituted or unsubstituted alkyl, substituted or unsubstituted alkenyl substituted or unsubstituted alkynyl; substituted or unsubstituted cycloalkyl, substituted or unsubstituted cycloalkenyl; substituted or unsubstituted aryl; substituted or unsubstituted arylalkyl; substituted or unsubstituted heteroaryl; substituted or unsubstituted heterocyclic; substituted or unsubstituted heterocycloalkyl; substituted or unsubstituted heteroarylalkyl.

In specific embodiments, GIZ compounds include GIZ, (5R,6R,7S,8S)-5-hydroxymethyl-2-octyl-5,6,7,8-tetrahydroimidazo[1,2-a]pyridine-6,7,8-triol and (5R,6R,7S, 8S)-5-Hydroxymethyl-2-(3,3-dimethylbutyl)-5,6,7,8-tetrahydroimidazo[1,2-a]pyridine-6,7,8-triol.

Synthesis of the foregoing can be achieved as follows:

a. (5R,6R,7S,8S)-5-Hydroxymethyl-2-n-octyl-5,6,7,8-tetrahydroimidazo[1,2-a]pyridine-6,7,8-triol ($IC_{50}$ for GCase=~0.07 nM)

A solution of (5R,6R,7S,8S)-6,7,8-Tris(benzyloxy)-5-[(benzyloxy)methyl]-2-(1-octynyl)-5,6,7,8-tetrahydroimidazo[1,2-a]pyridine (120 mg, 0.179 mmol) in THF/EtOH (2:1) (3 ml) is rapidly stirred with Pd(OH)2/C (0.1 g) under an atmosphere of hydrogen for 14 h. After filtration of the catalyst, the organic solution is concentrated on a rotovap and the residue is dissolved in CH2Cl2 (10 ml). The solution is cooled in an acetone-dry ice bath and a solution of BCl3 (1.0 M) in CH2Cl2 is slowly added. The reaction mixture is warmed room temperature and stirred for 3 hours. The reaction mixture is cooled in an ice-water bath, water added and for 0.5 hour. Most of the solvent is removed using a rotovap and the crude product is purified by chromatography ($CHCl_3$/MeOH/$H_2O$ 64:25:4). Lyophilization from water gives the title compound as white foam. $^1$H NMR (400 MHz, CD3OD): δ7.22 (s, 1H), 4.56 (d, 1H, J=8 Hz), 4.20-4.16 (m, 1H), 3.98-3.93 (m, 2H), 3.83 (t, 1H, J=8.4 Hz), 3.70 (dd, 1H, J=8.8 Hz and 10 Hz), 2.60 (t, 2H, J=7.2 Hz), 1.67-1.63 (m, 2H), 1.35-1.30 (m, 10H), 0.90 (t, 3H, J=6.8 Hz). MS (ES+): 313 [M+1].

b. (5R,6R,7S,8S)-6,7,8-Tris(benzyloxy)-5-[(benzyloxy)methyl]-2-(3,3-dimethylbyt-1-ynyl)-5,6,7,8-tetrahydroimidazo[1,2-a]pyridine ($IC_{50}$ for GCase=~1.1 nM)

In a similar manner to that described in a, (5R,6R,7S,8S)-6,7,8-Tris(benzyloxy)-5-[(benzyloxy)methyl]-2-iodo-5,6,7,8-tetrahydroimidazo[1,2-a]pyridine is converted to the title compound. $^1$H NMR (300 MHz, CDCl$_3$): δ7.41-7.14 (m, 20H), 7.13 (s, 1H), 5.10 (d, 1H, J=11.4 Hz), 4.81-4.66 (m, 3H), 4.62 (d, 1H, J=11.4 Hz), 4.49-4.42 (m, 3H), 4.18-4.13 (m, 1H), 4.11-4.06 (m, 2H), 3.84-3.77 (m, 2H), 3.71 (dd, 1H, J=4.8 Hz and 10.5 Hz), 1.31 (s, 9H). MS (ES+): 641 [M+1].

c. (5R,6R,7S,8S)-5-Hydroxymethyl-2-(3,3-dimethylbutyl)-5,6,7,8-tetrahydro-imidazo[1,2-a]pyridine-6,7,8-triol ($IC_{50}$ for GCase=~0.03 nM)

In a similar manner to that described in (b), (5R,6R,7S,8S)-6,7,8-Tris(benzyloxy)-5-[(benzyloxy)methyl]-2-(3,3-dimethylbyt-1-ynyl)-5,6,7,8-tetrahydro-imidazo[1,2-a]pyridine was converted to the title compound. $^1$H NMR (400 MHz, CD$_3$OD): δ6.97 (s, 1H), 4.41 (d, 1H, J=8 Hz), 4.09 (dd, 1H, J=2.4 Hz and 12 Hz), 3.86 (d, 1H, J=4.0 Hz and 12 Hz), 3.79-3.71 (m, 2H), 3.61 (dd, 1H, J=8.4 Hz and 9.2 Hz), 2.48-2.44 (m, 2H,), 1.50-1.47 (m, 2H), 0.89 (s, 9H). MS (ES+): 285 [M+1].

Polyhydroxylcycloalkylamines (PHCA) derivatives contemplated for use in the present invention include compounds represented by the following Formula III:

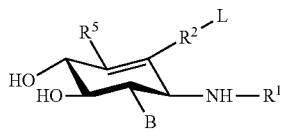

wherein B is selected from the group consisting of hydrogen, hydroxy, N-acetamino, and halogen.

$R^1$ is independently selected for each occurrence from the group consisting of hydrogen; substituted or unsubstituted alkyl, substituted or unsubstituted alkenyl, substituted or unsubstituted alkynyl, substituted or unsubstituted cycloalkyl substituted or unsubstituted cycloalkenyl, substituted or unsubstituted aryl, substituted or unsubstituted arylalkyl, substituted or unsubstituted heteroaryl, substituted or unsubstituted heterocyclic, substituted or unsubstituted heterocyclalkyl, substituted or unsubstituted heteroarylalkyl, —C(O)$R^3$ and —S(O)$_m R^3$, whereas m is 1 or 2, and $R^3$ is independently selected for each occurrence from the groups consisting of hydrogen, substituted or unsubstituted alkyl, substituted or unsubstituted alkenyl; substituted or unsubstituted alknyl; substituted or unsubstituted cycloalkyl, substituted or unsubstituted cycloalkenyl; substituted or unsubstituted aryl; substituted or unsubstituted arylalkyl; substituted or unsubstituted heteroaryl; substituted or unsubstituted heterocyclic; substituted or unsubstituted heterocyclyalkyl; substituted or unsubstituted heteroarylalkyl, and —C(O) attached to a $C_1$-$C_6$ substituted or unsubstituted alkyl.

$R^2$ optionally present is a short, flexible linker linear length of about 6 Å to about 12 Å, preferably, about 9 Å. $R^2$ can also be selected from the group consisting of $C_2$-$C_6$ substituted or unsubstituted alkyl optionally interrupted by one or more moieties chosen from the group consisting of NH, NHCOO, NHCONH, NHCSO, NHCSNH, CONH, NHCO, $NR^3$, O, S, S(O)$_m$ and —S(O)$_m NR^3$; $C_2$-$C_6$ substituted or unsubstituted alkenyl optionally interrupted by one or more moieties chosen from the group consisting of NH, NHCOO, NHCONH, NHCSO, NHCSNH, CONH, NHCO, $NR^3$, O, S, S(O)$_m$ and —S(O)$_m NR^3$; $C_2$-$C_6$ substituted or unsubstituted alkynyl optionally interrupted by one or more moieties chosen from the group consisting of NH, NHCOO, NHCONH, NHCSO, NHCSNH, CONH, NHCO, $NR^3$, O, S, S(O)$_m$ and —S(O)$_m NR^3$, whereas m is 1 or 2, and $R^3$ is independently selected for each occurrence from the groups consisting of hydrogen, substituted or unsubstituted alkyl, substituted or unsubstituted alkenyl; substituted or unsubstituted alknyl; substituted or unsubstituted cycloalkyl, substituted or unsubstituted cycloalkenyl; substituted or unsubstituted aryl; substituted or unsubstituted arylalkyl; substituted or unsubstituted heteroaryl; substituted or unsubstituted heterocyclic; substituted or unsubstituted heterocyclyalkyl; substituted or unsubstituted heteroarylalkyl, and —C(O) attached to a $C_1$-$C_6$ substituted or unsubstituted alkyl; and pharmaceutically acceptable salts and prodrugs thereof.

L is a lipophilic group selected from the group consisting of $C_3$-$C_{12}$ substituted or unsubstituted alkyl, substituted or unsubstituted alkenyl, substituted or unsubstituted alkynyl; substituted or unsubstituted cycloalkyl; substituted or unsubstituted cycloalkenyl; substituted or unsubstituted aryl; substituted or unsubstituted arylalkyl; substituted or unsubstituted heteroaryl; substituted or unsubstituted heterocyclic; substituted or unsubstituted heterocycloalkyl; substituted or unsubstituted heteroarylalkyl.

These compounds can be made according to the methods described in published U.S. patent application 2005/130972.

Hydroxylpiperidine derivatives contemplated for use in the present invention where Gba is mutated are represented by the following Formula IV.

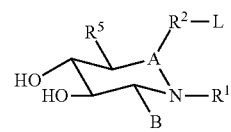

wherein A represents a carbon or nitrogen;

B is a hydrogen, hydroxyl, N-acetamide or a halogen;

$R^1$ is a hydrogen, substituted or unsubstituted: alkyl, alkenyl, alkynyl, cycloalkyl, cycloalkylalkyl, cycloalkenyl, aryl, arylalkyl, heteroaryl, heterocyclic, heterocyclyalkyl, or heteroarylalkyl; —C(O)$R^3$ or —S(O)$_m R^3$. Preferably, $R^1$ comprises H or an organic moiety having 1-12 carbon atoms.

$R^2$ is an optional short, flexible linker with a linear length of from about 6 Å to about 12 Å. Alternatively, $R^2$ is a $C_1$-$C_6$ substituted or unsubstituted: alkyl, alkenyl, or alkynyl optionally interrupted by one or more moieties chosen from the group consisting of NH, NHCOO, NHCONH, NHCSO, NHCSNH, CONH, NHCO, $NR^3$, O, S, S(O)$_m$ and —S(O)$_m NR^3$.

$R^3$ is of hydrogen, or a substituted or unsubstituted: alkyl, alkenyl; alknyl; cycloalkyl, cycloalkenyl; aryl; arylalkyl; heteroaryl; heterocyclic; heterocyclyalkyl; or heteroarylalkyl. Preferably, $R^3$ comprises H or an organic moiety having 1-12 carbon atoms, or more preferably 1-6 carbon atoms.

m is 1 or 2, and $R^5$ is a hydrogen, hydroxyl, or hydroxymethyl.

L is a hydrogen, lipophilic group having 1-12 carbon atoms comprising a substituted or unsubstituted: alkyl, alkenyl, alkynyl; cycloalkyl, cycloalkenyl; aryl; arylalkyl; heteroaryl; heterocyclic; heterocycloalkyl; or heteroarylalkyl.

In some embodiments, $R^2$ is selected from the group consisting of $C_2$-$C_6$ substituted or unsubstituted alkyl optionally interrupted by one or more moieties chosen from the group consisting of NH, $NR^3$, and O; $C_2$-$C_6$ substituted or unsubstituted alkenyl optionally interrupted by one or more moieties chosen from the group consisting of NH, $NR^3$ and O; $C_2$-$C_6$ substituted or unsubstituted alkenyl optionally interrupted by one or more heteroatoms chosen from the group consisting of NH, $NR^3$ and O; $C_2$-$C_6$ substituted or unsubstituted alkenyl optionally interrupted by one or more heteroatoms chosen from the group consisting of NH, $NR^3$ and O.

In other embodiments, $R^2$ is chosen from the group consisting of

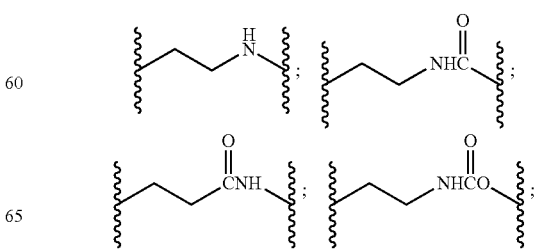

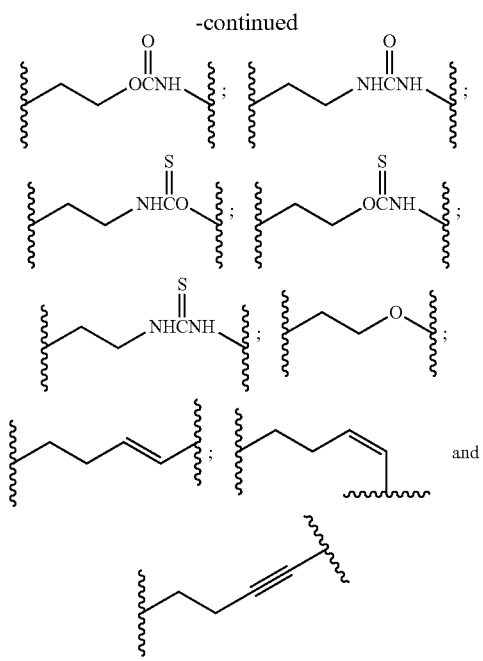

In other embodiments R² is not present and L is hydrogen, unsubstituted C₁-C₁₂ alkyl, or unsubstituted C₆-C₁₂ alkyl, such as an unsubstituted C₆ alkyl, unsubstituted C₇ alkyl, unsubstituted C₈ alkyl, C₉ alkyl or benzyl.

In specific embodiments, hydroxyl piperidine compounds contemplated for use in the invention are (3R,4R,5R,6S/6R)-5-(hydroxy methyl)-6-n-hexyl-3,4-dihydroxypiperidine; (3R,4R,5R,6S/6R)-5-(hydroxy methyl)-6-n-heptyl-3,4-dihydroxypiperidine; (3R,4R,5R,6S/6R)-5-(hydroxy methyl)-6-n-octyl-3,4-dihydroxypiperidine; and (3R,4R,5R,6S/6R)-5-(hydroxy methyl)-6-n-nonyl-3,4-dihydroxypiperidine.

In other specific embodiments, hydroxyl piperidine compounds contemplated for use in the present invention include but are not limited to the following: (3R,4R,5R,6S/6R)-5-(hydroxy methyl)-6-n-butyl-3,4-dihydroxypiperidine; (3R,4R,5R,6S/6R)-5-(hydroxy methyl)-6-n-hexyl-3,4-dihydroxypiperidine; (3R,4R,5R,6S/6R)-5-(hydroxy methyl)-6-n-heptyl-3,4-dihydroxypiperidine; (3R,4R,5R,6S/6R)-5-(hydroxy methyl)-6-n-octyl-3,4-dihydroxypiperidine; (3R,4R,5R,6S/6R)-5-(hydroxy methyl)-6-n-nonyl-3,4-dihydroxypiperidine; (3R,4R,5R,6S/6R)-5-(hydroxy methyl)-6-benzyl-3,4-dihydroxypiperidine.

Still other chaperones for GCase are described in U.S. Pat. No. 6,599,919 to Fan et al., and include calystegine A₃, calystegine A₅, calystegine B₁, calystegine B₂, calystegine B₃, calystegine B₄, calystegine C₁, N-methyl-calystegine B₂, DMDP, DAB, castanospermine, 1-deoxynojirimycin, N-butyl-deoxynojirimycin, 1-deoxynojirimycin bisulfate, N-butyl-isofagomine, N-(3-cyclohexylpropyl)-isofagomine, N-(3-phenylpropyl)-isofagomine, and N-((2Z,6Z)-3,7,11-trimethyldodeca-2,6,10-trienyl)-isofagomine.

Compounds of the present invention include pharmaceutically acceptable salts and pro-drugs of the above structures. Pharmaceutically acceptable salts include salts derived from inorganic bases such as Li, Na, K, Ca, Mg, Fe, Cu, Zn, Mn; salts of organic bases such as N,N'-diacetylethylenediamine, glucamine, triethylamine, choline, hydroxide, dicyclohexylamine, metformin, benzylamine, trialkylamine, thiamine; chiral bases like alkylphenylamine, glycinol, phenyl glycinol, salts of natural amino acids such as glycine, alanine, valine, leucine, isoleucine, norleucine, tyrosine, cystine, cysteine, methionine, proline, hydroxy proline, histidine, ornithine, lysine, arginine, serine; non-natural amino acids such as D-isomers or substituted amino acids; guanidine, substituted guanidine wherein the substituents are selected from nitro, amino, alkyl, alkenyl, alkynyl, ammonium or substituted ammonium salts and aluminum salts. Salts may include acid addition salts where appropriate which are, sulphates, nitrates, phosphates, perchlorates, borates, hydrohalides, acetates, tartrates, maleates, citrates, succinates, palmoates, methanesulphonates, benzoates, salicylates, benzenesulfonates, ascorbates, glycerophosphates, ketoglutarates. Pharmaceutically acceptable solvates may be hydrates or comprise other solvents of crystallization such as alcohols.

Prodrugs are compounds which are converted in vivo to active forms (see, e.g., R. B. Silverman, 1992, "The Organic Chemistry of Drug Design and Drug Action", Academic Press, Chp. 8). Prodrugs can be used to alter the biodistribution (e.g., to allow compounds which would not typically enter the reactive site of the protease) or the pharmacokinetics for a particular compound. For example, a carboxylic acid group, can be esterified, e.g., with a methyl group or an ethyl group to yield an ester. When the ester is administered to a subject, the ester is cleaved, enzymatically or non-enzymatically, reductively, oxidatively, or hydrolytically, to reveal the anionic group. An anionic group can be esterified with moieties (e.g., acyloxymethyl esters) which are cleaved to reveal an intermediate compound which subsequently decomposes to yield the active compound.

Examples of prodrugs and their uses are well known in the art (See, e.g., Berge et al. (1977) "Pharmaceutical Salts", J. Pharm. Sci. 66:1-19). The prodrugs can be prepared in situ during the final isolation and purification of the compounds, or by separately reacting the purified compound with a suitable derivatizing agent. For example hydroxy groups can be converted into esters via treatment with a carboxilic acid in the presence of a catalyst. Examples of cleavable alcohol prodrug moieties include substituted and unsubstituted, branched or unbranched lower alkyl ester moieties, (e.g., ethyl esters), lower alkenyl esters, di-lower alkyl-amino lower-alkyl esters (e.g., dimethylaminoethyl ester), acylamino lower alkyl esters, acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides.

Formulation, Dosage, and Administration of Specific Pharmacological Chaperones

The present invention provides that the specific pharmacological chaperone be administered in a dosage form that permits systemic administration, since the compounds need to cross the blood-brain barrier to exert effects on neuronal cells. In one embodiment, the specific pharmacological chaperone is administered as monotherapy, preferably in an oral dosage form (described further below), although other dosage forms are contemplated. The oral administration includes daily administration in divided doses, or controlled-release formulations, or by less frequent administration of immediate- or sustained-release dosage forms. Formulations, dosage, and routes of administration for the specific pharmacological chaperone are detailed below.

Formulations

The specific pharmacological chaperone can be administered in a form suitable for any route of administration, including e.g., orally in the form tablets or capsules or liquid, or in sterile aqueous solution for injection. When the specific pharmacological chaperone is formulated for oral administration, the tablets or capsules can be prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or another suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled or sustained release of the specific pharmacological chaperone.

The pharmaceutical formulations of the specific pharmacological chaperone suitable for parenteral/injectable use generally include sterile aqueous solutions (where water soluble), or dispersions and sterile powders for the extemporaneous preparation of sterile injectable solutions or dispersion. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be brought about by various antibacterial and antifungal agents, for example, parabens, chlorobutanol, phenol, benzyl alcohol, sorbic acid, and the like. In many cases, it will be reasonable to include isotonic agents, for example, sugars or sodium chloride. Prolonged absorption of the injectable compositions can be brought about by the use in the compositions of agents delaying absorption, for example, aluminum monosterate and gelatin.

Sterile injectable solutions are prepared by incorporating the specific pharmacological chaperone in the required amount in the appropriate solvent with various of the other ingredients enumerated above, as required, followed by filter or terminal sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The formulation can contain an excipient. Pharmaceutically acceptable excipients which may be included in the formulation are buffers such as citrate buffer, phosphate buffer, acetate buffer, and bicarbonate buffer, amino acids, urea, alcohols, ascorbic acid, phospholipids; proteins, such as serum albumin, collagen, and gelatin; salts such as EDTA or EGTA, and sodium chloride; liposomes; polyvinylpyrrolidone; sugars, such as dextran, mannitol, sorbitol, and glycerol; propylene glycol and polyethylene glycol (e.g., PEG-4000, PEG-6000); glycerol; glycine or other amino acids; and lipids. Buffer systems for use with the formulations include citrate; acetate; bicarbonate; and phosphate buffers. Phosphate buffer is a preferred embodiment.

The formulation can also contain a non-ionic detergent. Preferred non-ionic detergents include Polysorbate 20, Polysorbate 80, Triton X-100, Triton X-114, Nonidet P-40, Octyl α-glucoside, Octyl β-glucoside, Brij 35, Pluronic, and Tween 20.

Administration

The route of administration of the specific pharmacological chaperone may be oral (preferably) or parenteral, including intravenous, subcutaneous, intra-arterial, intraperitoneal, ophthalmic, intramuscular, buccal, rectal, vaginal, intraorbital, intracerebral, intradermal, intracranial, intraspinal, intraventricular, intrathecal, intracisternal, intracapsular, intrapulmonary, intranasal, transmucosal, transdermal, or via inhalation.

Administration of the above-described parenteral formulations of the specific pharmacological chaperone may be by periodic injections of a bolus of the preparation, or may be administered by intravenous or intraperitoneal administration from a reservoir which is external (e.g., an i.v. bag) or internal (e.g., a bioerodable implant). See, e.g., U.S. Pat. Nos. 4,407,957 and 5,798,113, each incorporated herein by reference. Intrapulmonary delivery methods and apparatus are described, for example, in U.S. Pat. Nos. 5,654,007, 5,780,014, and 5,814,607, each incorporated herein by reference. Other useful parenteral delivery systems include ethylene-vinyl acetate copolymer particles, osmotic pumps, implantable infusion systems, pump delivery, encapsulated cell delivery, liposomal delivery, needle-delivered injection, needle-less injection, nebulizer, aerosolizer, electroporation, and transdermal patch. Needle-less injector devices are described in U.S. Pat. Nos. 5,879,327; 5,520,639; 5,846,233 and 5,704,911, the specifications of which are herein incorporated by reference. Any of the formulations described above can be administered using these methods.

Subcutaneous injections have the advantages allowing self-administration, while also resulting in a prolonged plasma half-life as compared to intravenous administration. Furthermore, a variety of devices designed for patient convenience, such as refillable injection pens and needle-less injection devices, may be used with the formulations of the present invention as discussed herein.

Dosage

The amount of specific pharmacological chaperone effective to rescue the endogenous mutant Lysosome enzyme can be determined on a case-by-case basis by those skilled in the art. Pharmacokinetics and pharmacodynamics such as half-life ($t_{1/2}$), peak plasma concentration ($C_{max}$), time to peak plasma concentration ($t_{max}$), exposure as measured by area under the curve (AUC), and tissue distribution for both the replacement protein and the specific pharmacological chaperone, as well as data for specific pharmacological chaperone/Lysosome enzyme binding (affinity constants, association and dissociation constants, and valency), can be obtained using ordinary methods known in the art to determine compatible amounts required to stabilize the replacement protein, without inhibiting its activity, and thus confer a therapeutic effect.

Data obtained from cell culture assay or animal studies may be used to formulate a therapeutic dosage range for use in humans and non-human animals. The dosage of compounds used in therapeutic methods of the present invention preferably lie within a range of circulating concentrations that includes the $ED_{50}$ concentration (effective for 50% of the tested population) but with little or no toxicity. The particular dosage used in any treatment may vary within this range, depending upon factors such as the particular dosage form employed, the route of administration utilized, the conditions of the individual (e.g., patient), and so forth.

A therapeutically effective dose may be initially estimated from cell culture assays and formulated in animal models to achieve a circulating concentration range that will be both above the $EC_{50}$ observed in cells for a period of time, and below the observed $IC_{50}$ for a period of time. The $EC_{50}$ concentration of a compound is the concentration that achieves a half-maximal increase in enzyme activity (e.g., as determined from the cell culture assays), which the $IC_{50}$ is the concentration which achieve half-maximal inhibition of enzyme activity. Appropriate dosages for use in a particular individual, for example in human patients, may then be more accurately determined using such information as described further below.

Measures of compounds in plasma may be routinely measured in an individual such as a patient by techniques such as high performance liquid chromatography (HPLC) or gas chromatography.

Toxicity and therapeutic efficacy of the composition can be determined by standard pharmaceutical procedures, for example in cell culture assays or using experimental animals to determine the $LD_{50}$ and the $ED_{50}$. The parameters $LD_{50}$ and $ED_{50}$ are well known in the art, and refer to the doses of a compound that is lethal to 50% of a population and therapeutically effective in 50% of a population, respectively. The dose ratio between toxic and therapeutic effects is referred to as the therapeutic index and may be expressed as the ratio: $LD_{50}/ED_{50}$. Specific pharmacological chaperones that exhibit large therapeutic indices are preferred.

Where the chaperone is an inhibitor, the optimal doses of the specific pharmacological chaperone are determined according to the amount required to stabilize the GCase, e.g., lysosomal enzyme, in vivo, in tissue or circulation, without sustaining inhibition of the enzyme. This will depend on the bioavailability of the specific pharmacological chaperone in tissue or in circulation, and on the pharmacokinetics and pharmacodynamics of the specific pharmacological chaperone in tissue or in circulation, for a prolonged period of time. For, the concentration of the inhibitor can be determined by calculating the $EC_{50}$ and $IC_{50}$ values of the specific chaperone for the enzyme so that the dose administered would both (i) achieve a plasma concentration above the $EC_{50}$ for some time to permit maximum trafficking to the lysosome, and (ii) permit the plasma concentration to fall below the $IC_{50}$ for some time once the enzyme is in the lysosome so substrate can be hydrolyzed.

This determination also will depend on pharmacokinetic factors including the half-life of the chaperone in blood and tissue, Tmax, and Cmax, and the half-life of the lysosomal enzyme. In one embodiment, rationales for estimating dosing regimens for pharmacological chaperones are described further in U.S. provisional patent application 60/914,288, filed on Apr. 27, 2007, which is incorporated by reference herein in its entirety. This application describes "peak and trough" dosing for GCase inhibitors where an initial "loading dose" is given daily to maximize stabilization of the enzyme and trafficking to the lysosome, followed by a period of non-daily interval dosing in which permits dissociation of the inhibitor and hydrolysis of the substrate. However, other dosing regimens also are contemplated.

Combination Drug Therapy

The pharmacological chaperone can be used to treat patients with the neurological diseases in combination with other drugs that are also used to treat the disorder. Conventional drug treatments for Parkinson's disease include but are not limited to; RNAi, and pharmacological agents such as levodopa, anticholinergics, COMT (Catechol-O-methyl transferase) inhibitors, dopamine receptor agonists, MAOI (monoamine oxidase inhibitors), peripheral decarboxylase inhibitors.

The pharmacological chaperone or chaperones for GCase also can be used to treat patients with Niemann-Pick Type C disease in combination with allopregnanolone, a low-cholesterol diet, or cholesterol-lowering agents such as the statins (e.g., Lipitor®); fibrates such as fenofibrate (Lipidil®); niacin; ezetimibe (Zetia®) and/or binding resins such as cholestyramine (Questran®).

In addition, the pharmacological chaperone can be used in combination with gene therapy. Gene therapy is contemplated both with replacement genes such as Gba or with inhibitory RNA (siRNA) for the SNCA gene. Gene therapy is described in more detail in commonly-owned patent application Ser. No. 10/781,356, filed on Feb. 17, 2004.

Other contemplated combination therapy includes combinations of specific pharmacological chaperones with vaccine therapy, such a vaccine comprising α-syn and an adjuvant (Pilcher et al., Lancet Neurol. 2005; 4(8):458-9), or combinations of GCase chaperones with chaperones for α-syn, such as Hsp70 or a specific pharmacologic chaperone, combinations with anti-inflammatory agents such as ibuprofen or other NSAIDS, or with other agents that may be protective in neurodegenerative diseases such as dextromethorphan (Li et al., FASEB J. 2005; April; 19(6):489-96), genistein (Wang et al., Neuroreport. 2005; Feb. 28; 16(3):267-70), or minoclycline (Blum et al., Neurobiol Dis. 2004; December; 17(3): 359-66).

Also contemplated is combination therapy with a substrate inhibitor for GCase, such as N-butyl-deoxynojirimycin (Zavesca®).

Lastly, combinations of GCase chaperones with one or more chaperones for other lysosomal enzymes is also contemplated In one embodiment, the chaperones are administered to an individual who does not have any mutations in any of the lysosomal enzymes for which chaperones are administered. In another embodiment, the individual has a mutation in a lysosomal enzyme other than GCase and is administered a specific chaperone for that enzyme in combination with the GCase chaperone. Following is a Table which lists potential chaperones for lysosomal enzymes.

TABLE 1

| LYSOSOMAL ENZYME | SPECIFIC PHARMACOLOGICAL CHAPERONE |
|---|---|
| α-Glucosidase<br>GenBank Accession No. Y00839 | 1-deoxynojirimycin (DNJ)<br>α-homonojirimycin<br>castanospermine |
| Acid β-Glucosidase (β-glucocerebrosidase)<br>GenBank Accession No. J03059 | isofagomine<br>C-benzyl isofagomine and derivatives<br>N-alkyl(C9-12)-DNJ<br>Glucoimidazole (and derivatives)<br>C-alkyl-IFG (and derivatives)<br>N-alkyl-β-valeinamines<br>Fluphenozine<br>calystegines $A_3$, $B_1$, $B_2$ and $C_1$ |
| α-Galactosidase A<br>GenBank Accession No. NM000169 | 1-deoxygalactonojirimycin (DGJ)<br>α-allo-homonojirimycin<br>α-galacto-homonojirimycin<br>β-1-C-butyl-deoxynojirimycin<br>calystegines $A_2$ and $B_2$<br>N-methyl calystegines $A_2$ and $B_2$ |
| Acid β-Galactosidase<br>GenBank Accession No. M34423 | 4-epi-isofagomine<br>1-deoxygalactonojirimycin |
| Galactocerebrosidase (Acid β-Galactosidase)<br>GenBank Accession No. D25283 | 4-epi-isofagomine<br>1-deoxygalactonojirimycin |
| Acid α-Mannosidase<br>GenBank Accession No. U68567 | 1-deoxymannojirimycin<br>Swainsonine<br>Mannostatin A |
| Acid β-Mannosidase<br>GenBank Accession No. U60337 | 2-hydroxy-isofagomine |
| Acid α-L-fucosidase<br>GenBank Accession No. NM_000147 | 1-deoxyfuconojirimycin<br>β-homofuconojirimycin<br>2,5-imino-1,2,5-trideoxy-L-glucitol<br>2,5-deoxy-2,5-imino-D-fucitol<br>2,5-imino-1,2,5-trideoxy-D-altritol |
| α-N-Acetylglucosaminidase<br>GenBank Accession No. U40846 | 1,2-dideoxy-2-N-acetamido-nojirimycin |
| α-N-Acetylgalactosaminidase<br>GenBank Accession No. M62783 | 1,2-dideoxy-2-N-acetamido-galactonojirimycin |
| β-Hexosaminidase A<br>GenBank Accession No. NM_000520 | 2-N-acetylamino-isofagomine<br>1,2-dideoxy-2-acetamido-nojirimycin<br>nagstatin |
| β-Hexosaminidase B<br>GenBank Accession No. NM_000521 | 2-N-acetamido-isofagomine<br>1,2-dideoxy-2-acetamido-nojirimycin<br>nagstatin |
| α-L-Iduronidase<br>GenBank Accession No. NM_000203 | 1-deoxyiduronojirimycin<br>2-carboxy-3,4,5-trideoxypiperidine |
| β-Glucuronidase<br>GenBank Accession No. NM_000181 | 6-carboxy-isofagomine<br>2-carboxy-3,4,5-trideoxypiperidine |
| Sialidase<br>GenBank Accession No. U84246 | 2,6-dideoxy-2,6, imino-sialic acid<br>Siastatin B |
| Iduronate sulfatase<br>GenBank Accession No. AF_011889 | 2,5-anhydromannitol-6-sulphate |
| Acid sphingomyelinase<br>GenBank Accession No. M59916 | desipramine, phosphatidylinositol-4,5-diphosphate |

In one specific embodiment, Niemann-Pick Type C disease is treated with a specific pharmacological chaperone for GCase in combination with a specific pharmacological chaperone for β-hexosaminidase A and/or a specific pharmacological chaperone for acid β-galactosidase, since this disease is characterized by accumulation of $G_{M2}$-gangliosides and $G_{M1}$-gangliosides in addition to GlcCer (Vanier et al., *Brain Pathology*. 1998; 8: 163-74).

Determining Responses to Chaperone Therapy

As indicated above, patients with neurodegenerative diseases characteristic neurological symptoms. For example, patients having Parkinson's disease experience tremor, rigidity, bradykinesia, and postural imbalance. Patients having Lewy Body Dementia experience strong psychotic symptoms (visual hallucinations) in addition to mental decline such as memory loss and an inability to carry out simple tasks. Observable improvements in symptoms with pharmacological chaperone therapy, or a delay of onset of certain symptoms in patients at risk of developing a disorder, or a delay in progression of the disorder will be evidence of a favorable response to the chaperone therapy.

In addition, measurable surrogate markers also may be useful for evaluating response to chaperone therapy. For instance, some investigators have reported detecting higher levels of α-syn or oligomeric forms of α-syn have been detected in the plasma of patients with Parkinson's disease (Lee et al., *J Neural Transm*. 2006; 113(10):1435-9; El-Agnaf et al., *FASEB J*. 2006; 20(3):419-25), while some have reported decreased plasma α-syn in Parkinson's patients compared with normal controls (Li et al., Exp Neurol. 2007; 204(2):583-8).

EXAMPLES

The present invention is further described by means of the examples, presented below. The use of such examples is illustrative only and in no way limits the scope and meaning of the invention or of any exemplified term. Likewise, the invention is not limited to any particular preferred embodiments described herein. Indeed, many modifications and variations of the invention will be apparent to those skilled in the art upon reading this specification. The invention is therefore to be limited only by the terms of the appended claims along with the full scope of equivalents to which the claims are entitled.

Example 1

In Vivo GCase Activity in Mice Upon Treatment with IFG

One GCase chaperone, IFG, was administered to normal mice expressing wild-type GCase and GCase activity was evaluated.

Methods

Drug Administration.

This Example provides information on the effects of isofagomine, a GCase-specific chaperone on mice. IFG were administered to the mice at 200 mg/kg/day; organs and plasma were collected 4 weeks after initiation of the study. Ten male C57BL6 (25 g) mice per group were used. The drug was be given in the drinking water, therefore water consumption was monitored daily.

In the control group (0 mg/kg/day), the mice were dosed daily in the drinking water (no drug) and divided into two groups. Ten animals were euthanized after 4 weeks of treatment, blood was collected from the descending aorta or vena cava, and tissues were harvested and then necropsied.

In the test group, 10 mice were dosed daily in the drinking water with an administration aim of 200 mg/kg/day.

The blood samples were drawn into lithium heparin and spun for plasma. After bleeding, the spleen, lung, brain and liver were removed and placed into vials. The vials were put into dry ice for rapid freezing. The tissues and plasma were then analyzed for tissue levels of GCase.

Tissue Preparation.

Small portions of tissue were removed and added to 500 μl lysis buffer (20 mM sodium citrate and 40 mM disodium hydrogen phosphate, pH 4.0, including 0.1% Triton X-100). Tissues were then homogenized using a microhomogenizer for a brief time, followed by centrifugation at 10,000 rpm for 10 minutes at 4° C. Supernatants were transferred to a new tube and used for the enzyme assay.

Tissue Enzyme Assay.

To 2.5 μl of supernatant (in 96-well plates) was added 17.5 μl reaction buffer (citrate phosphate buffer, pH 4.5, no Triton X-100), and 50 μl of 4-methyl umbelliferone (4-MU)-labeled substrate, β-glucopyranoside, or a labeled negative controls (α-glucopyranoside or α-galacatopyranoside). Plates were incubated at 37° for 1 hour, followed by the addition of 70 μl stop buffer (0.4 M glycine-NaOH, pH 10.6). Activity of GCase was determined by measuring the emission at 460 nm by exciting at 355 nm using a 1 second read time per well (Victor2 multilabel counter-Wallac) Enzyme activity was normalized to the amount in μl of lysate added, and enzyme activity per μl of lysate was estimated. The enhancement ratio is equal to the activity with the compound over the activity without the compound.

Results

Figure 1:
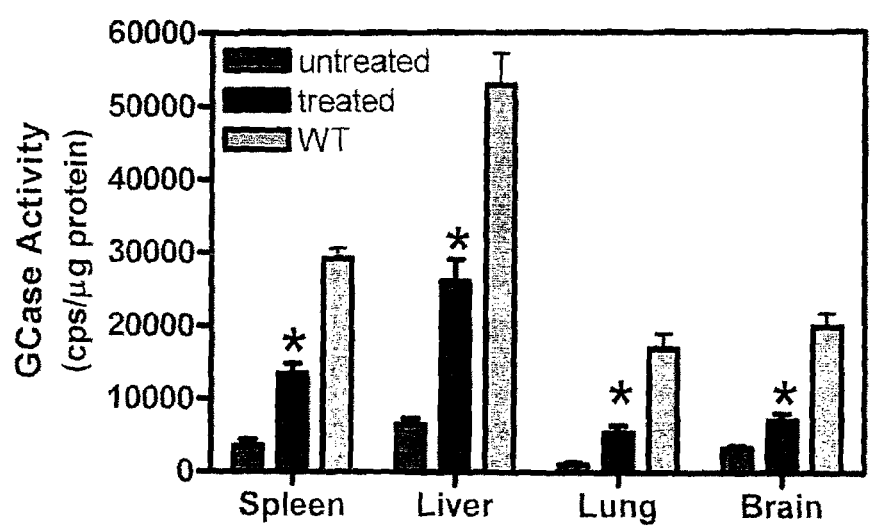
FIG. 1.

As demonstrated in FIG. 1, GCase levels were increased following two weeks of treatment with IFG in the liver (1), spleen (2), brain (3) and lung (4). Similar results were observed in a separate experiment where 10 mice each were treated with 0, 1, 10, or 100 mg/kg/day IFG free base; wild-type GCase activity exhibited a linear dose-response increase with IFG free base.

These results support confirm that the specific pharmacological chaperones can increase the activity of non-mutant GCase in vivo, and particularly in the brain.

These results support confirm that the specific pharmacological chaperones can increase the activity of non-mutant GCase in vivo, and particularly in the brain.

Example 2

Administration of Multiple-Doses of IFG to Evaluate Safety, Tolerability, Pharmacokinetics and Effect on β-Glucocerebrosidase Enzymatic Activity It was previously shown that DGJ, a pharmacological chaperone for α-galatosidase A, another lysosomal enzyme, produced a dose-dependent increase in α-galactosidase A activity in white blood cells of healthy volunteers at 50 mg b.i.d. and 150 mg b.i.d.

This example describes two double-blind placebo-controlled Phase I study of oral dosing of IFG to to evaluate the safety, tolerability, pharmacokinetics, and pharmacodynamics of IFG in healthy volunteers.

Study Design and Duration.

In a first-in-human single ascending dose study (1a), doses of 8, 25, 75, 150 (two cohorts), and 300 mg were administered (6 active, 2 placebo in each cohort). In a multiple ascending dose study (1b), doses of 25, 75, and 225 mg were administered daily for seven days (6 active, 2 placebo in each cohort). In both studies, of the eight subjects in each group; six were randomized to receive IFG tartrate, and two subjects received placebo. Subjects were confined from the evening of day-1 until 24 hrs after completion of dosing. In the phase 1a study subjects returned at 48 hrs (PK sampling) and 7 days (safety follow-up) following dosing. In the phase 1b study subjects returned at 48 h (PD sampling), 7 days (PD sampling and safety follow-up), and 14 days (PD sampling) following the last dose Study Population.

Subjects were healthy male and female volunteers between 19 and 55 years of age (inclusive) consisting of members of the community at large.

Safety and Tolerability Assessments.

Safety was determined by evaluating vital signs, laboratory parameters (serum chemistry, hematology, and urinalysis), physical examination and by recording adverse events during the Treatment Period.

Pharmacokinetic Sampling.

Blood samples (10 mL each) were collected in blood collection tubes containing EDTA before dosing was determined at regular intervals for the phas 1a during 48 hr following dosing. In the phase 1b study a full IFG tartrate pharmacokinetic profile was determined for 24 hr following the first dose, Cmin values were obtained pre-dose on day 6 and 7, and another full profile was determined for 24 hr following the final, day 7, dose.

GCase Enzymatic Activity Sampling

GCase activity was determined pre-dose on days 1, 3, 5, 7, 9, 14, and 21. Blood samples were cooled in an ice bath and centrifuged under refrigeration as soon as possible. Plasma samples were divided into two aliquots and stored at 20±10° C. pending assay. At the end of the study, all samples were transferred to MDS Pharma Services Analytical Laboratories (Lincoln) for analysis. The complete urine output was collected from each subject for analysis of IFG to determine renal clearance for the first 12 hours after adiministration of IFG tartrate on days 1 and 7.

Statistical Analysis.

Safety data including laboratory evaluations, physical exams, adverse events, ECG monitoring and vital signs assessments were summarized by treatment group and point of time of collection. Descriptive statistics (arithmetic mean, standard deviation, median, minimum and maximum) were calculated for quantitative safety data as well as for the difference to baseline. Frequency counts were compiled for classification of qualitative safety data.

Results

Pharmacokinetics.

In both studies, isofagomine tartrate was generally well tolerated at all doses and treatment-emergent adverse events in both studies were mostly mild. No serious adverse events occurred.

Isofagomine tartrate showed good systemic exposure via the oral route. In the single-dose study, plasma AUC and Cmax values were linearly correlated with administered dose. Mean plasma levels peaked at 3.4 hr. (SEM: 0.6 hr.) and the plasma elimination half-life was 14 hr. (SEM: 2 hr.). In the multiple-dose study, after 7 days of oral administration, the pharmacokinetic behavior was found to be linear with dose, with no unexpected accumulation of isofagomine tartrate. Tmax and half-life values were similar to those observed in the single-dose study.

After repeated doses of 25 to 225 mg of IFG were administered to healthy male and female subjects, the mean half-lives ranged from 5.14 to 19.9 hours. Minimal accumulation of IFG was observed after repeated doses, based on AUC and Cmax comparisons on Day 1 and Day 7. There were no observable sex differences in any pharmacokinetic parameters evaluated.

The adverse events most frequently reported by healthy adult subjects who received IFG included contact dermatitis, headache, nausea, increased serum bilirubin, dizziness, scab, ocular hyperaemia, and puncture site pain. No serious adverse events occurred and no subject discontinued treatment due to an adverse event.

GCase Activity.

In all subjects receiving IFG, there was a marked increase in GCase levels during the treatment period, followed by a decrease upon removal of the drug and a return to near baseline levels by day 21, two weeks after the last dose of IFG. The increases in enzyme levels were dose-related, reaching approximately 3.5-fold above baseline (FIG. 2). These results indicate that orally administered IFG has the potential to increase the levels of its intended target, GCase, in vivo in humans.

Example 3

Evaluation of IFG in Transgenic Mice Overexpressing α-Synuclein

This example describes results from administration of IFG to transgenic mice over-expressing α-synuclein. Neuronal expression of wild-type human α-synuclein resulted in progresssive accumulation of α-synuclein, and ubiquinated immunoreactive inclusions, including nuclear and cytoplasmic, in neurons in the neocortex, CA3 hippocampus, and substantia nigra by age two months (Masliah et al., *Science*. 2000; 287: 1269). Based on the ability of IFG to increase the activity of wild-type GCse in mice and humans, it was anticipated that increasing GCase in these mice might compensate for the over-expressed α-synuclein and reduce or eliminate inclusions.

Methods

Mice.

48 transgenic animals (male and female) were allocated to 6 groups (n=8) at an age of 5 to 6 weeks concerning baseline and 3 to 4 weeks, respectively concerning all other treatment groups at treatment start. One group of transgenic animals served as baseline group (5 weeks old) and was sacrificed untreated on day 0. One group of transgenic animals was treated with vehicle.

Treatment.

Mice (ages 3-4 weeks) were treated once daily (orally) at either 2 mg/kg; 20 mg/kg; or 200 mg/kg of IFG tartrate for 3 months. One group also was treated once every other day at 20 mg/kg.

Tissue Preparation.

Animals of the baseline group were sacrificed at an age of 5 weeks. All other animals were sacrificed at the end of the 3 months treatment period and blood for preparation of serum and macrophages as well as lung, brain and CSF were extracted. Therefore, all mice were sedated by standard inhalation anesthesia (Isofluran, Baxter). Cerebrospinal fluid was obtained by blunt dissection and exposure of the foramen magnum. Upon exposure, a Pasteur pipette was inserted to the approximate depth of 0.3-1 mm into the foramen magnum. CSF was collected by suctioning and capillary action until flow fully ceases. CSF was immediately frozen and kept at −80° C.

After CSF sampling, each mouse was placed in dorsal recumbence, the thorax was opened and a 26-gauge needle attached to a 1 cc syringe was inserted into the right cardiac ventricular chamber. Light suction was applied to the needle. Blood was separated into 2 parts. One part was collected in 3.8% sodium citrate to obtain plasma and macrophages, one part to obtain serum. Mice were transcardially perfused with physiological (0.9%) saline and lung tissue as well as brain was rapidly removed. The lungs were rinsed in cold PBS (outside only) to remove blood and then they were quick frozen.

The brains were removed and hemisected. The right hemispheres of all mice were immersion fixed in freshly produced 4% paraformaldehyde/PBS (pH 7.4) for one hour at room temperature. Thereafter brains were transferred to a 15% sucrose PBS solution for 24 hours to ensure cryoprotection. On the next day brains were frozen in liquid isopentane and stored at −80° C. until used for histological investigations. To determine the effects of the IFG-tartrate treatment from 8 animals per group 10 μm-thick cryosections were cut for determination of alpha-synuclein pathology. All organs and tissues mentioned were sampled and from specific brain regions i.e. hippocampus, midbrain, frontal cortex and striatum of one hemibrain were extracted and frozen. The other brain half was processed for histological evaluation.

Staining.

For evaluation of the number of α-synuclein positive cells and Lewy body like inclusions an immunohistochemical staining was carried out using the monoclonal human alpha-synuclein specific antibody (Alexis®; Cat #804-258-L001), dilution 1:5, detected with secondary Cy2 antibody (Jackson Immunoresearch®). The number of alpha-synuclein positive cells in five different layers, one slice per layer, was counted for evaluation in the whole hippocampus and cortex separately.

Briefly, samples were washed for 10 min with PBS at room temperature, followed by fixing for 30 min at room temperature with 4% paraformaldehyde, followed by washing 2 times for 5 min each with PBS at room temperature. For Proteinase K-treated sections, sections were incubated in PBS containing 10 μg/ml proteinase-K for 10 minutes at room temperature. Next, samples were incubated for 15 min at room temperature with blocking solution to block endogenous peroxidase, followed by two more 5 min washes with PBS. Samples were then incubated for 60 min at room temperature with a blocking reagent to block non-specific binding, followed by two more 5 min washes with PBS. Samples were then incubated with M.O.M. diluent for 5 min at room temperature, followed by incubation with the primary antibody (dilution 1:5 in M.O.M. diluent) for 60 min with at room temperature.

After an hour, samples were washed 2 times for 5 min with PBS at room temperature, and incubated for another 60 min at room temperature with blocking reagent. Following two washes, samples were incubated with with secondary Ab Cy 2-Goat Anti-Rat (Dilution 1:200 in M.O.M.) for 60 minutes at room temperature, in the absence of light. Samples were then washed for 5 min with PBS, for 5 min with sterile, molecular-biology grade water, and covered with polyvinyl alcohol.

Determination of Brain α-Synuclein Pathology.

For evaluation of the α-synuclein immunoreactivity, specialized image analysis software (Image Pro Plus, version 4.5.1.29) was used. Each fluorescence image was recorded using the same exposure time set to 400 ms. Up to 100 single images with 100-fold magnification each were assembled to one image (real size about 3×1 m), assuring a high pixel resolution for the IR count. All assembled images were contrasted manually and for detection in all measurements, the same intensity based threshold was used. A size restriction to a minimal size of 30 $\mu m^2$ was set to be sure to count a single cell in the very acuity layer and only once among the adjacent layers. During the macro based rating procedure the outlines of the object counts were saved.

In a further step, all measured objects were extracted from the original (contrast free) image using the saved outlines and assembled according to object size in a sorted object image. The sorted object images were re-evaluated using a roundness restriction (lower limit: 1; upper limit: 1.5) to part α-synuclein positive cells from bias objects. These automatic object counts were visually controlled and the count manually corrected by adding all explicit cells not being round enough or not separable from background in the spread sheet, leading to the ultimate cell count.

The following parameters were evaluated and calculated:
measurement area of the cortex and the hippocampus in each slice; and
number of IR positive cells per measurement area of the specific brain regions hippocampus and cortex Results Qualitative.

Figure 3:
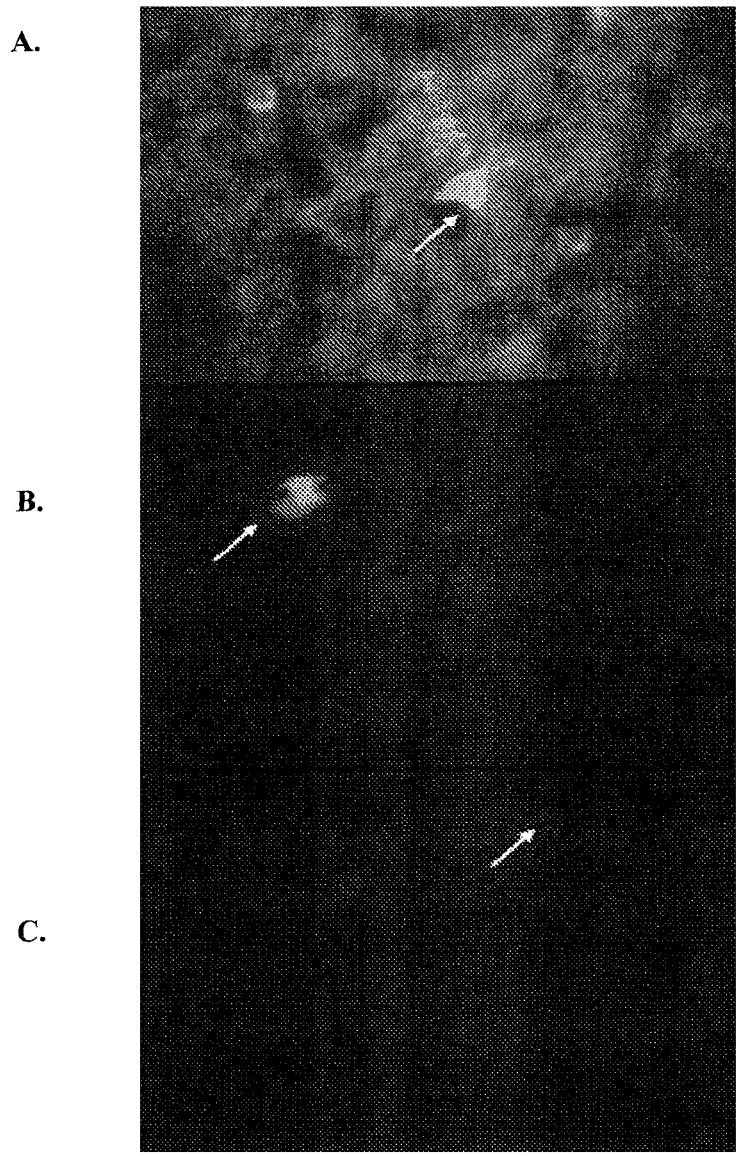
FIG. 3 shows results of immunohistochemical staining for α-synuclein in the cortex of transgenic mice over-expressing α-synuclein either treated or untreated with IFG tartrate.
Figure 4:
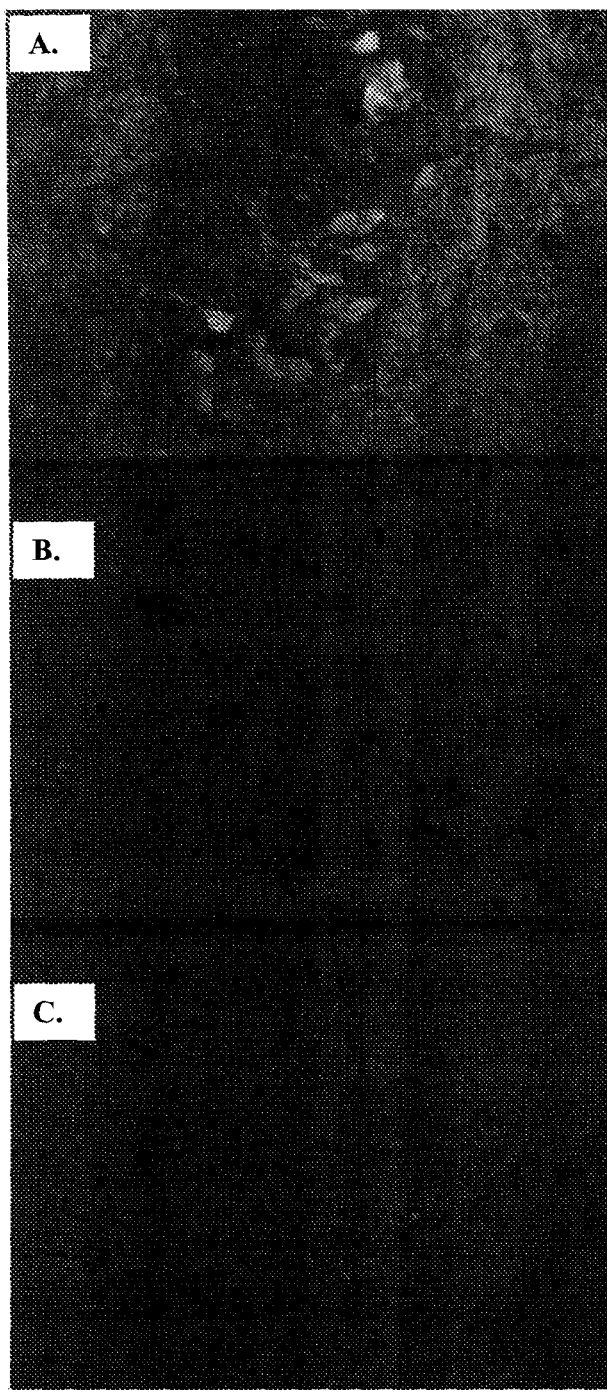
FIG. 4 shows qualitative results of immunohistochemical staining for α-synuclein in the hippocampus of transgenic mice over-expressing α-synuclein either treated or untreated with IFG tartrate.

Differences between treated and untreated mice were qualitatively visible in different degrees from strongly decreased background and decreased α-synuclein positive cell numbers in some of the IFG-tartrate (2 and 20 mg/kg b.w. daily) treated animals, to background reduction without decreased immunoreactive cell numbers, as compared to the pathology of control animals (FIGS. 3A-C, cortex; FIGS. 4A-C, hippocampus). The intensity of background in human α-synuclein overexpressing mice derives from intracellular α-synuclein in neuritic and dendritic processes as well as synapses, therefore a reduction of background is equatable to a reduction of protein expression in these neuronal structures.

Figure 5:
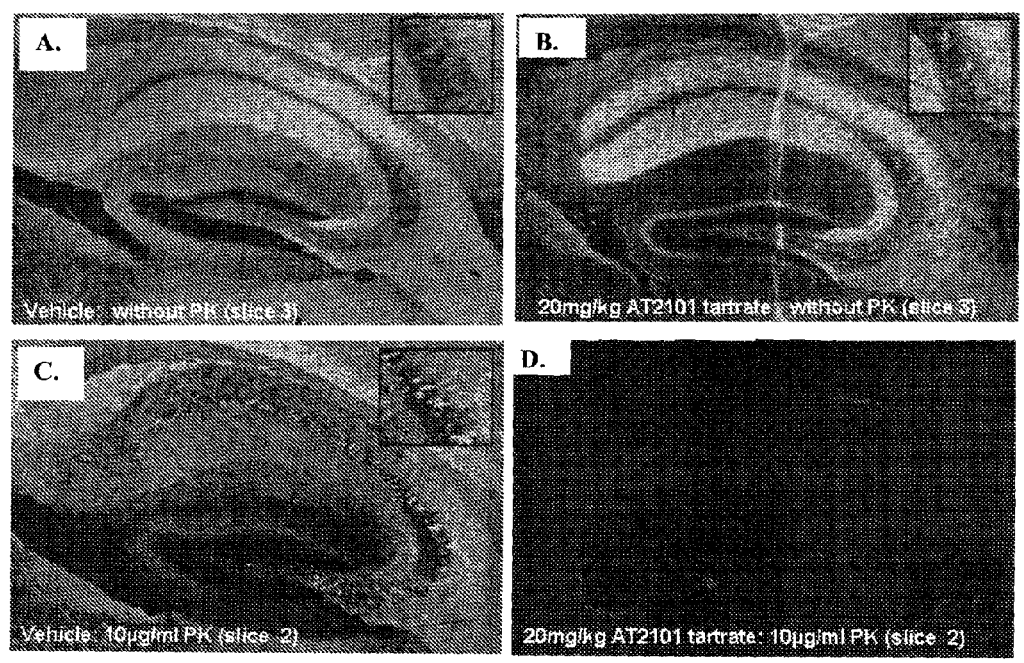
FIG. 5 shows qualitative results of immunohistochemical staining for α-synuclein in samples pre-treated with Proteinase K from the brain of one transgenic mouse.

This is the first demonstration that this mouse model develops aggregated α-synuclein, as evidenced by staining of sections from a mouse treated with a vehicle control (FIG. 5A). Pre-treatment of sections with Proteinase-K prior to staining for α-synuclein also reveals the presence of aggregated α-synuclein by digestion of monomeric α-synuclein (FIG. 5C). Pre-treatment of the mouse with IFG appears to reduce the α-synuclein aggregation. The image represents analysis of only a single animal to date that responded to 20 mg/kg IFG-tartrate in the absence or presence of pre-treatment with Proteinase K (FIGS. 5B and D, respectively). Since α-synuclein aggregates are resistant to Proteinase K digestion, the pre-treatment reveals that aggregates of α-synuclein accumulate in this animal model over the time frame investigated, and that treatment with IFG-tartrate in the 3 months prior to sacrifice prevents the accumulation of these α-synuclein aggregates.

Quantitative.

Figure 6:
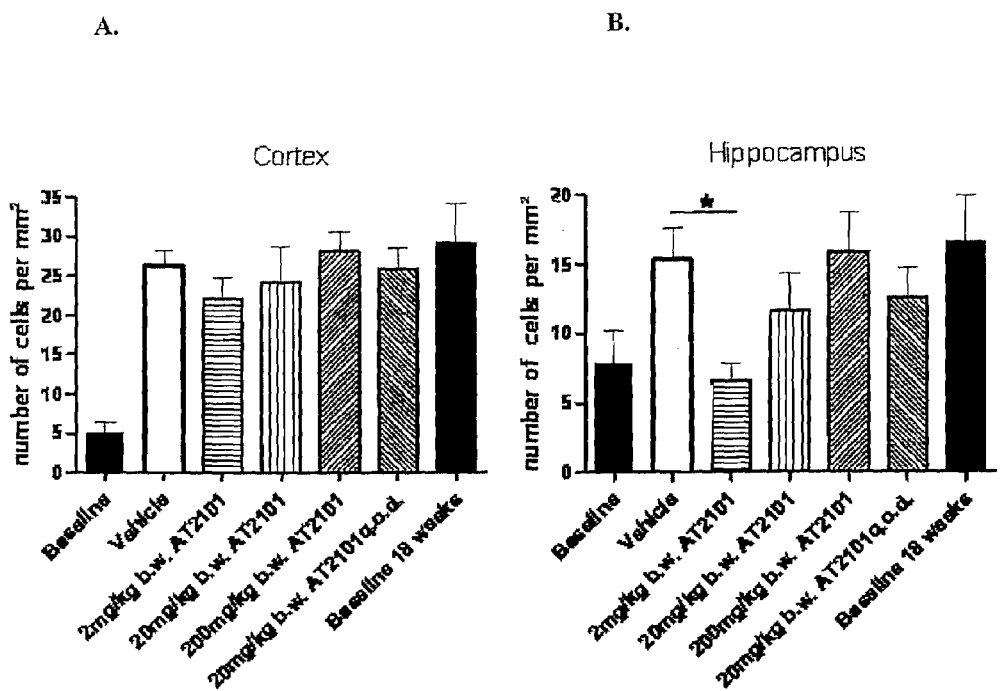
FIG. 6 shows quantitative results of immunohistochemical staining for α-synuclein in the cortex (A) and hippocampus (B) of transgenic mice over-expressing α-synuclein either treated or untreated with IFG at the indicated concentrations for 3 months. The number of α-synuclein positive cells per $mm^2$ was evaluated.

The treatment with IFG-tartrate led to decreased α-synuclein pathology in both measured brain regions, however the effect was more pronounced in the hippocampus (FIG. 5B) and did not reach significance level in the cortex (FIG. 6A). The dose response was clearly visible in the hippocampus and potentially in the cortex. The lowest dose, 2 mg IFG-tartrate/kg, was the most effective and reduced the number of immunoreactive cells in the hippocampus significantly versus vehicle-treated controls ($p<0.05$) (FIG. 6B). Higher dosage did not lead to statistical significant reduction of α-synucleinpathology. There was no difference between a daily or every other day treatment with 20 mg IFG-tartrate, and the mean was on the same level. However, it must be stated that the 20 mg dose was not effective versus controls and therefore the result that each or every other day treatment has the same effectiveness may not be accurate.

The evaluations in the baseline group led to following results: First, at the age of five weeks there was variation in individual mice regarding appearance of α-synuclein filled cells in the hippocampus, leading to variation of hippocampal pathology and high statistical standard deviation. In addition, the number of immunoreactive cells in the cortex was consistently low at this age. Therefore, the increase of pathology during ageing was significant versus all investigated groups in the cortex, but did not reach significance level in the hippocampus due to the individual differences in this region in the baseline group.

After averaging both regions to an individual mean, equal to increasing the total investigated volume per animal, all groups had significantly higher α-synuclein positive cell load versus baseline ($p<0.01$) except mice treated with most effective dose, 2 mg IFG-tartrate ($p>0.05$). This allows the conclusion that the dosage of 2 mg IFG-tartrate/kg prevented mice from the age-accompanied increase of pathology.

These data support that increasing GCase may decrease α-synuclein levels and prevent aggregation of α-synuclein monomers into oligomeric aggregates. Further supporting for this finding comes from recent results in which elevated levels of plasma α-syn (as detected by ELISA) were observed in patients having Gaucher disease (i.e., having decreased GCase activity) compared to normal controls ($p=0.027$).

Plasma from fifty-three males and females with Gaucher disease (including one male with Type 3) were evaluated.

Example 4

Accumulation of α-Synuclein and the Development of a Parkinsonism Behavioral Phenotype in the Brains of Mice with Reduced GCase Activity This example describes results from immunohistochemical analyses of alpha-synuclein in the brains of transgenic mutant knock-in mice with reduced GCase activity and V394L homozygous knock-in mice treated with conduritol-β-epoxide (CBE) an irreversible inhibitor of GCase. Transgenic mouse models which have reduced GCase activities and accumulate glucosylceramide (Sun et al 2005, Journal of lipid research) in the brain, also accumulated ubiquitinated and aggregated α-synulcein. A transgenic mouse model for Gaucher disease has been developed which do not accumulate glucosylceramide or α-synuclein in the brain, but which could be induced to accumulate glucosylceramide and α-synuclein by treatment with conduritol-β-epoxide (CBE), an irreversible inhibitor of GCase.

Methods

Mice.

Mice homozygous for the point mutations D409H or V394L and expressing a low level of saposin C in a prosaposin knock-out background, were analyzed for accumulation of α-synuclein in the brain. These mice have been reported to accumulate glucosylceramide in the brain. Mice homozygous for the point mutations V394L only, were analyzed for α-synuclein accumulation with and without CBE treatment. These mice do not accumulate glucosylceramide in the brain unless treated with CBE. Mice were administered CBE daily by interperitonally injection for 30 consequitive days (500 µM calculated from the total weight of the mouse) and brains were analyzed by immunohistochemistry for accumulation of α-synuclein.

Tissue Preparation and Staining.

Brain tissue was frozen and fixed for immunohistochemistry with 4% paraformaldehyde and serial sections were co-labelled with anti-human α-synuclein (ab1903; Abcam, Cambridge, Mass.) and rabbit anti-ubiquitin (ab7780; Abcam, Cambridge, Mass.).

Results

Serieal sections from the brains of mice having a combined Gba mutation (D409H or V394L) with reduced expression of the GCase-activating protein prosaposin C were stained for α-synuclein and ubiquitin. In 10-wk old mice, a significant number of α-synuclein aggregates were observed in hippocampus, basal ganglia (caudate, putamen, substantia nigra, subthalamic nucleus), brain stem, and some cortical and cerebellar regions. Ubiquitinated aggregates were also found in these regions and some co-localized with α-synuclein. However, α-synuclein aggregates were not observed in V394L mice (with normal prosaposin). Treatment of the V394L mice with CBE for 30 days, however, resulted in accumulation of α-synuclein in the brain. Combined, these results suggest that reducing GCase activity and increasing glucosylceramide levels in the brain may lead to an increase in α-synuclein accumulation.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, product descriptions, and protocols are cited throughout this application, the disclosures of which are incorporated herein by reference in their entireties for all purposes.

What is claimed:

1. A method for treating an alpha-synucleinopathy in an individual having or at risk of developing an alpha-synucleinopathy, wherein the individual does not have a mutation in the gene encoding beta-glucocerebrosidase, comprising administering to the individual (i) a pharmacological chaperone that binds to beta-glucocerebrosidase in an amount effective to treat the alpha-synucleinopathy, wherein treating the alpha-synucleinopathy comprises increasing the activity of β-glucocerebrosidase and thereby modulate the levels of alpha-synuclein and (ii) a second therapeutic agent, wherein the pharmacological chaperone is an isofagomine compound or derivative thereof.

2. The method of claim 1, wherein the second therapeutic agent is a substrate inhibitor for GCase.

3. The method of claim 2, wherein the substrate inhibitor is N-butyldeoxynojirimycin.

4. The method of claim 1, wherein the second therapeutic agent is an anti-inflammatory agent.

5. The method of claim 4, wherein the anti-inflammatory agent is ibuprofen or other NSAID.

6. The method of claim 1, wherein the second therapeutic agent is dextromethorphan, genistein, or minocycline.

7. The method of claim 1, wherein the second therapeutic agent is selected from the group consisting of RNAi, levodopa, an anticholinergic, a Catechol-O-methyl transferase inhibitor, a dopamine receptor agonist, a monoamine oxidase inhibitor, and a peripheral decarboxylase inhibitor.

8. The method of claim 1, wherein the second therapeutic agent comprises inhibitory RNA (siRNA) for the SNCA gene.

9. The method of claim 1, wherein the second therapeutic agent comprises gene therapy for the GBA gene.

10. The method of claim 1, wherein the second therapeutic agent is a pharmacological chaperone for another lysosomal enzyme.

11. The method of claim 1, wherein the second therapeutic agent is a vaccine comprising alpha-syn and an adjuvant.

12. The method of claim 1, wherein the second therapeutic agent is a chaperone for alpha-syn.

13. The method of claim 12, wherein the chaperone for alpha-syn is Hsp70.

14. The method of claim 1, wherein the pharmacological chaperone is a competitive inhibitor of β-glucocerebrosidase.

15. The method of claim 1, wherein the pharmacological chaperone is isofagomine tartrate.

16. The method of claim 1, wherein the α-synucleinopathy is selected from the group consisting of Parkinson's disease, Lewy Body Disease, Multiple System Atrophy, Hallervorden-Spatz disease, and Frontotemporal Dementia.

17. The method of claim 1, wherein the α-synucleinopathy is Parkinson's disease.

\* \* \* \* \*